(12) United States Patent
Goede et al.

(10) Patent No.: US 10,204,708 B2
(45) Date of Patent: Feb. 12, 2019

(54) SYSTEM AND METHOD FOR DERIVING PARAMETERS FOR HOMEOSTATIC FEEDBACK CONTROL OF AN INDIVIDUAL

(71) Applicant: Agency for Science, Technology and Research, Singapore (SG)

(72) Inventors: Sam L. Goede, Stompetoren (NL); Johannes W. Dietrich, Hattingen (DE); Khee Shing Melvin Leow, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 479 days.

(21) Appl. No.: 14/443,276

(22) PCT Filed: Dec. 5, 2013

(86) PCT No.: PCT/SG2013/000515
§ 371 (c)(1),
(2) Date: May 15, 2015

(87) PCT Pub. No.: WO2014/088516
PCT Pub. Date: Jun. 12, 2014

(65) Prior Publication Data
US 2015/0339458 A1 Nov. 26, 2015

(30) Foreign Application Priority Data

Dec. 5, 2012 (SG) ................................ 201208940-5

(51) Int. Cl.
*G06F 17/10* (2006.01)
*G16H 50/50* (2018.01)
(Continued)

(52) U.S. Cl.
CPC ............. *G16H 50/50* (2018.01); *A61B 5/145* (2013.01); *A61B 5/7275* (2013.01); *G01N 33/76* (2013.01); *G01N 33/78* (2013.01); *G06F 17/10* (2013.01)

(58) Field of Classification Search
None
See application file for complete search history.

(56) References Cited

U.S. PATENT DOCUMENTS

2004/0133355 A1* 7/2004 Schneider ............. G06N 3/126
702/19
2009/0280575 A1 11/2009 Chen et al.
(Continued)

FOREIGN PATENT DOCUMENTS

CN 101516255 A 8/2009
CN 102472744 A 5/2012
(Continued)

OTHER PUBLICATIONS

Leow A Mathematical Model of Pituitary-Thyroid Interaction to Provide an Insight into the Nature of the Thyrotropin-Thyroid Hormone Relationship Journal of Theoretical Biology 248, 2007, pp. 275-287.*
(Continued)

*Primary Examiner* — Aniss Chad
*Assistant Examiner* — Cuong V Luu
(74) *Attorney, Agent, or Firm* — Wolf, Greenfield & Sacks, P.C.

(57) ABSTRACT

A method and system of deriving a physiological homeostatic operating set point of an individual comprising the steps of: obtaining a dataset of predetermined number of homeostatic measurements of the individual; fitting the dataset of predetermined number of homeostatic measurements according to a negative exponential decay function;
(Continued)

identifying and setting the physiological homeostatic operating set point unique to the individual as the point corresponding to the point of maximum curvature on the fitted negative exponential decay function is disclosed. The method is especially suited for determining the [FT4]-[TSH] set point, which is unique for each individual.

12 Claims, 16 Drawing Sheets

(51) Int. Cl.
    *A61B 5/145*      (2006.01)
    *A61B 5/00*      (2006.01)
    *G01N 33/76*      (2006.01)
    *G01N 33/78*      (2006.01)

(56) References Cited

U.S. PATENT DOCUMENTS

| | | | |
|---|---|---|---|
| 2011/0052715 A1* | 3/2011 | Davis | A61K 41/0038 424/499 |
| 2016/0041153 A1* | 2/2016 | Brown | G01N 33/5308 435/7.23 |

FOREIGN PATENT DOCUMENTS

| | | |
|---|---|---|
| WO | WO 2012/009483 A1 | 1/2012 |
| WO | WO 2014/088516 A1 | 6/2014 |

OTHER PUBLICATIONS

Degon et al. A Quantitative Model of the Human Thyroid: Development and Observations American Control Conference, Jun. 2005, pp. 961-966.*

Chinese Office Action dated Jul. 25, 2016 for Application No. CN 201380063408.7.

Leow, A mathematical model of pituitary-thyroid interaction to provide an insight into the nature of the thyrotropin-thyroid hormone relationship. J Theor Biol. Sep. 21, 2007;248(2):275-87. Epub May 18, 2007.

Pandiyan et al., A patient-specific model of the negative-feedback control of the hypothalamus-pituitary-thyroid (HPT) axis in autoimmune (Hashimoto's) thyroiditis. Math Med Biol. Sep. 2014;31(3):226-58. doi: 10.1093/imammb/dqt005. Epub May 2, 2013.

Extended European Search Report dated Jul. 5, 2016 for Application No. EP 13860303.0.

International Search Report and Written Opinion dated Feb. 26, 2014 for Application No. PCT/SG2013/000515.

International Preliminary Report on Patentability dated Jun. 18, 2015 for Application No. PCT/SG2013/000515.

Andersen et al., Narrow individual variations in serum T(4) and T(3) in normal subjects: a clue to the understanding of subclinical thyroid disease. J Clin Endocrinol Metab. Mar. 2002;87(3):1068-72.

Benhadi et al., Pilot study on the assessment of the setpoint of the hypothalamus-pituitary-thyroid axis in healthy volunteers. Eur J Endocrinol. Feb. 2010;162(2):323-9. doi: 10.1530/EJE-09-0655. Epub Nov. 19, 2009.

Dietrich et al., TSH and Thyrotropic Agonists: Key Actors in Thyroid Homeostasis. J Thyroid Res. 2012;2012:351864. doi: 10.1155/2012/351864. Epub Dec. 30, 2012.

Goede et al., General error analysis in the relationship between free thyroxine and thyrotropin and its clinical relevance. Comput Math Methods Med. 2013;2013:831275. doi: 10.1155/2013/831275. Epub Sep. 8, 2013.

EP 13860303.0, Jul. 5, 2016, Extended European Search Report.
PCT/SG2013/000515, Feb. 26, 2014, International Search Report and Written Opinion.
PCT/SG2013/000515, Jun. 18, 2015, International Preliminary Report on Patentability.

* cited by examiner

Fig 4a Rsq = 99.5%     Fig 4b Rsq = 97.3%

Fig 4c Rsq = 79.6%     Fig 4d Rsq = 97.4%

Fig 5a Rsq = 99.5%   Fig 5b Rsq = 99.1%

Fig 5c Rsq = 99.8 %   Fig 5d Rsq = 51.9 %

Fig.5a-d Calculated pituitary curves from 4 patients from dataset 2 (Bergmansheil University Hospitals Bochum)

SYSTEM AND METHOD FOR DERIVING PARAMETERS FOR HOMEOSTATIC FEEDBACK CONTROL OF AN INDIVIDUAL

CROSS-REFERENCE TO RELATED APPLICATION

This application claims priority to Singapore patent application SG 201208940-5, the entire contents of which are incorporated herein by reference.

FIELD OF THE INVENTION

The present invention relates to a system and method for deriving parameters for homeostatic feedback control of an individual. The system and method are particularly suited, but not limited to determine the homeostatic operating set point of an individual and will be described in this context.

BACKGROUND ART

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

Under normal conditions, the thyroid gland produces certain predetermined amounts of thyroid hormones as thyroxin (hereinafter referred to as [T4]), and tri-iodothyronine (hereinafter referred to as [FT3]) for proper regulation of body functions. In physiology, the main thyroid component to be regulated is the free form of [T4] called free thyroxin (hereinafter referred to as [FT4]). This regulation mechanism is known to operate according to a negative feedback process. The level of [FT4] is closely monitored by the hypothalamus pituitary (hereinafter referred to as HP) unit.

Hypothyroidism and hyperthyroidism are caused by an impaired function of the thyroid gland and manifest as an imbalance in the production of thyroid hormones. It afflicts a range of mammals including, but not limited to humans. Hence the term 'patient(s)' or 'individual(s)' afflicted by thyroid disease resulting in thyroid hormonal imbalance may refer to any mammal that is affected. Hypothyroidism results from under-activity of the thyroid with a decrease in production of thyroid hormones and hyperthyroidism results from over-activity of the thyroid with an increase in production of thyroid hormones. It is known that the HP compares the level of the [FT4] in the blood stream with a predetermined level or set point. The HP may stimulate the thyroid to produce more or less [FT4] by means of the thyroid stimulating hormone, the hormone hereinafter referred to as [TSH]. To illustrate, if the level of [FT4] exceeds the set point level, the stimulation of [TSH] will be reduced. When the detected level of [FT4] is below the set point level, the amount of [TSH] will be increased to keep the level of [FT4] as close as possible to the set point value. This negative feedback regulation mechanism is characterized by the relationship between [FT4] and [TSH].

There has been ongoing research on the relationship between [FT4] and [TSH]. Nevertheless, most current research assumes the physiological homeostatic operating set point as a relatively constant value which does not vary much across individuals.

Despite existing research on set point and the HPT system, there are currently no well-defined standards or methods for accurately defining or predicting the physiological homeostatic operating set point of a given individual, in particular the optimal set point correlating the optimal [TSH] and [FT4] levels for different individuals. There also exists a need to fine-tune the mathematical models to account for variation between the physiological homeostatic operating set point of different individuals, the result of the same which may be used for clinical applications.

The present invention seeks to provide a system and method that meet the above needs at least in part.

SUMMARY OF THE INVENTION

The inventors have discovered that optimal levels of thyrotropin (thyroid stimulating hormone, [TSH]) and the corresponding level of free thyroxin (free T4) varies for each unique individual. This is a paradigm shift from the existing assumption that the physiological homeostatic operating set point is similar across most individuals.

The normal reference interval of [TSH] and [FT4] values falls within a "knee" region (i.e. defined as the region with maximum curvature on a graphical plot depicting the relationship between [TSH] and [FT4]). The optimal [TSH]-[FT4] set point unique to each individual is coincidentally also found at the "knee" region. This suggests an evolutionary survival advantage conferred by nature on most vertebrates to respond and calibrate their [TSH] output robustly to achieve tight homeostasis equilibrium of their [FT4] levels within a narrow physiological window.

The graphical plot, typically in the form of a negative exponential model is further developed to characterize the relationship between homeostatic measurements (in particular but not limited to the relationship between [FT4] and [TSH]) as characterised in the following aspects of the present invention.

In accordance with a first aspect of the present invention, there is provided a method of deriving a physiological homeostatic operating set point of an individual comprising the steps of: obtaining a dataset of predetermined number of homeostatic measurements of the individual; fitting the dataset of predetermined number of homeostatic measurements according to a negative exponential decay function; and identifying and setting the physiological homeostatic operating set point unique to the individual as the point corresponding to the point of maximum curvature on the fitted negative exponential decay function.

Preferably, each of the predetermined number of homeostatic measurements is a thyroid-stimulating hormone [TSH] level and a corresponding free thyroxin [FT4] level of the individual, the homeostatic measurements obtained under controlled predetermined measurement conditions.

Preferably, the negative exponential decay function is mathematically expressed as the following formula:

$$[TSH] = \frac{S}{\exp(\varphi[FT4])}$$

wherein S is a multiplier parameter; $\varphi$ is a rotational parameter; and exp denotes the exponential function.

Preferably, the parameters S and $\varphi$ are calculated from a first and a second homeostatic measurements of the individual according to the following formula:

$$\varphi = \left(\frac{1}{[FT4]_1 - [FT4]_2}\right) \ln\left(\frac{[TSH]_2}{[TSH]_1}\right)$$

$$S = [TSH]_1 \exp(\varphi[FT4]_1) = [TSH]_2 \exp(\varphi[FT4]_2)$$

where the subscript 1 and 2 denote the first and second homeostatic measurement respectively.

Preferably, the physiological homeostatic operating set point of the individual is determined according to the following formula:

$$[FT4]_{SP} = \frac{\ln(S\varphi\sqrt{2})}{\varphi}$$

$$[TSH]_{SP} = \frac{1}{\varphi\sqrt{2}}$$

Where $[FT4]_{SP}$ and $[TSH]_{SP}$ denote the physiological homeostatic operating set point of the individual.

Preferably, the step of fitting the dataset of predetermined number of homeostatic measurements is based on interpolation, smoothing or extrapolation techniques.

Preferably, the method further includes the step of filtering any outlier data from the dataset of predetermined number of homeostatic measurements before the step of fitting the dataset.

Preferably, the method further includes a step of validating the fitted negative exponential decay function using a goodness of fit test (Rsq) comparing with at least three homeostatic measurements.

Preferably, subsequent to the second homeostatic measurement, the parameters S and φ are iteratively fine-tuned by using each subsequent homeostatic measurement with the first and second homeostatic measurements.

Preferably, the point corresponding to the physiological homeostatic operating set point of the individual is where the value of the first derivative of TSH with respect to FT4 is $$\frac{d[TSH]}{d[FT4]} = \frac{-1}{\sqrt{2}} = -0.707$$

Preferably, the negative exponential decay function is modified to take into account hysteresis effect in accordance with the following mathematical expression:—

$$[TSH] = \frac{S}{\alpha S + \exp(\varphi[FT4])}$$

and the parameter α defines the maximum [TSH] secretion from anterior pituitary under conditions of complete hypothyroidism.

Preferably, the method further comprises the step of validating the physiological homeostatic operating set point of the individual based on a control system model.

Preferably, the method comprises an additional step of calculating the loop gain of the obtained physiological homeostatic operating set point mathematically expressed as:—

$$G_L = \frac{A\varphi}{e}$$

Where $G_L$ is the calculated loop gain; e is the exponential constant e≈2.718;

$$A = \frac{[FT4]_{setpoint}}{0.632};$$

and $[FT4]_{setpoint}$ is the obtained [FT4] level of the operating set point for the individual, and accepting the obtained physiological homeostatic operating set point if the calculated $G_L$ is greater than 1.

As an alternative to the [TSH]-[FT4] measurement, each of the predetermined number of homeostatic measurements comprises a thyroid-stimulating hormone [TSH] level and a corresponding triiodothyronine [T3] level.

Preferably, each homeostatic measurement is obtained by measuring the amount of a homeostatic amino acid expression product with a detection reagent capable of hybridizing to the homeostatic amino acid expression product.

Preferably, the detection reagent comprises an antibody and a detectable marker.

Preferably, the antibody is capable of hybridizing to a thyroid-stimulating hormone.

Preferably, the antibody is capable of hybridizing to a free thyroxin.

Preferably, the method further comprises the step of administering a therapeutically effective amount of a compound that is able to adjust the homeostatic measurements of the individual to the calculated physiological homeostatic operating set point unique to the individual.

Preferably, the therapeutically effective compound comprises thyroxin.

Preferably, the therapeutically effective amount of a compound comprises active iodothyronines or iodothyroacetic acids.

In accordance with a second aspect of the invention there is provided a computer readable medium containing software instructions that when executed by a computer cause the computer to perform the method as provided in the first aspect of the invention.

In accordance with a third aspect of the invention there is provided a system for deriving a physiological homeostatic operating set point of an individual comprising a processing unit operable to obtain a dataset of predetermined number of homeostatic measurements of the individual and fit the dataset of predetermined number of homeostatic measurements according to a negative exponential decay function; wherein the processing unit is further operable to identify and set the physiological homeostatic operating set point unique to the individual as the point corresponding to the point of maximum curvature on the fitted negative exponential decay function.

Preferably, each of the predetermined number of homeostatic measurements is the thyroid-stimulating hormone (TSH) level and the corresponding free thyroxin (FT4) level when the individual is fully controlled under predetermined measurement conditions.

Preferably, the negative exponential decay function is mathematically expressed as the following formula:

$$[TSH] = \frac{S}{\exp(\varphi[FT4])}$$

Wherein S is a multiplier parameter and φ is a rotational parameter; exp denotes the exponential constant e≈2.718.

Preferably, the parameters S and φ are calculated from a first and a second homeostatic measurements of the individual according to the following formula:

$$\varphi = \left(\frac{1}{[FT4]_1 - [FT4]_2}\right) \ln\left(\frac{[TSH]_2}{[TSH]_1}\right)$$

$$S = [TSH]_1 \exp(\varphi[FT4]_1) = [TSH]_2 \exp(\varphi[FT4]_2)$$

where the subscript 1 and 2 denote the first and second homeostatic measurement respectively.

Preferably, the point of maximum curvature corresponding to the physiological homeostatic operating set point of the individual is determined according to the following formula:

$$[FT4]_{SP} = \frac{\ln(S\varphi\sqrt{2})}{\varphi}$$

$$[TSH]_{SP} = \frac{1}{\varphi\sqrt{2}}$$

where $[FT4]_{SP}$ and $[TSH]_{SP}$ denote the physiological homeostatic operating set point of the individual.

As an alternative to the [TSH]-[FT4] measurement each of the predetermined number of homeostatic measurements comprises a thyroid-stimulating hormone (TSH) level and a corresponding triiodothyronine (T3) level.

Preferably, the dataset is fitted based on non-linear regression or a non-linear method of least squares related to an exponential function.

Preferably, the dataset is filtered to remove any outlier data from the dataset of predetermined number of homeostatic measurements before fitting.

Preferably, the fitted negative exponential decay function is validated using a goodness of fit test (Rsq) comparing at least three distinctly separated sets of homeostatic measurements under predetermined and controlled conditions.

Preferably, subsequent to the second homeostatic measurement, the parameters S and φ are iteratively fine-tuned by using each subsequent distinctly separated sets of [FT4] and [TSH] measurements.

Preferably, the point corresponding to the physiological homeostatic operating set point of the individual is where the value of the first derivative of TSH with respect to FT4 is:

$$\frac{d[TSH]}{d[FT4]} = \frac{-1}{\sqrt{2}} = -0.707$$

Preferably, the processing unit is operable to validate of the obtained physiological homeostatic operating set point of the individual based on a control system model.

Preferably, the processing unit operable to calculate the loop gain of the obtained physiological homeostatic operating set point mathematically expressed as $$G_L = \frac{A\varphi}{e}$$

Where $G_L$ is the calculated loop gain; e is the exponential constant ≈ 2.718;

$$A = \frac{[FT4]_{setpoint}}{0.632};$$

and $[FT4]_{setpoint}$ is the obtained [FT4] level of the operating set point for the individual; the processing unit operable to accept the obtained physiological homeostatic operating set point if the calculated $G_L$ is greater than 1.

Preferably, the negative exponential decay function is modified to take into account hysteresis effect in accordance with the following mathematical expression:—

$$[TSH] = \frac{S}{\alpha S + \exp(\varphi[FT4])}$$

and the parameter α defines the maximum [TSH] secretion from anterior pituitary under conditions of complete hypothyroidism.

Preferably, a homeostatic measurement is obtained by measuring the amount of a homeostatic amino acid expression product with a detection reagent capable of hybridizing to the homeostatic amino acid expression product.

Preferably, the detection reagent comprises an antibody and a detectable marker.

Preferably, the antibody is capable of hybridizing to a thyroid-stimulating hormone.

Preferably, the antibody is capable of hybridizing to a free thyroxin.

Preferably, the system further comprises a means of adjusting the homeostatic measurements of the individual to the calculated physiological homeostatic operating set point unique to the individual using a therapeutically effective amount of a compound able to adjust the homeostatic measurements of the individual.

Preferably, the therapeutically effective amount of a compound comprises thyroxin.

Preferably, the therapeutically effective amount of a compound comprises active iodothyronines or iodothyroacetic acids.

BRIEF DESCRIPTION OF THE DRAWINGS

The present invention will now be described, by way of example only, with reference to the accompanying drawings, in which.

Other arrangements of the invention are possible and, consequently, the accompanying drawings are not to be understood as superseding the generality of the preceding description of the invention.

PREFERRED EMBODIMENTS OF THE INVENTION

Knowledge of the unique individualized set point is expected to tailor diagnostic cut-offs of thyroid hormonal disorders and improve accuracy of dosing of levothyroxin (L-T4) substitution and anti-thyroid drug therapy.

In accordance with an embodiment of the invention there is provided a method 10 of deriving a physiological homeostatic characteristic curve of an individual. The method 10 comprises the following steps:
a. obtaining a dataset 12 of predetermined number of homeostatic measurements of the individual (step 102);
b. fitting the dataset 12 of predetermined number of homeostatic measurements according to a negative exponential decay function 14 (step 108); wherein the negative exponential decay function 14 comprises at least two parameters unique to the individual.

The dataset 12 may be formed with at least three measurements (step 104). It is to be appreciated that more measurements would result in a more accurate curve fitting according to the negative exponential decay function 14.

The method 10 may include a step of filtering outliers from the dataset 12 (step 106) which precedes step 108. The step of filtering of outliers from the dataset 12 is performed in accordance with principles of data selection as commonly known to a person skilled in the art.

The method 10 is particularly suited to derive the hypothalamus pituitary (HP) characteristic of the individual. The HP characteristic of, individual relates the level of thyroid-stimulating hormone [TSH] level in milliunits per liter (mU/L) and the corresponding free thyroxin [FT4] level in picomoles per liter (pmol/L) in the individual. In the following description, homeostatic measurements would be understood to refer to measurements of the level of [TSH] and corresponding [FT4] in an individual.

The inventors have formulated the relationship between [FT4] and [TSH] as a parameterized negative exponential model (hereinafter referred to as PNEM), with at least two independent model parameters S and φ which characterizes the [FT4]-[TSH] relationship on an individual level.

The relationship is mathematically expressed with the following formula:

$$[TSH] = \frac{S}{\exp(\varphi[FT4])} \quad (1)$$

Where S is a multiplier parameter and φ is a rotational (exponential) parameter; exp denotes the exponential function $e^x$, where e is the exponential constant having a value of approximately 2.718.

Based on empirical tests, equation (1) is valid between the following ranges:—
0.01<[TSH]<50 mU/L; and
5<[FT4]<40 pmol/L.

It is to be appreciated that the parameters S and φ are unique to the individual.

Figure 1:
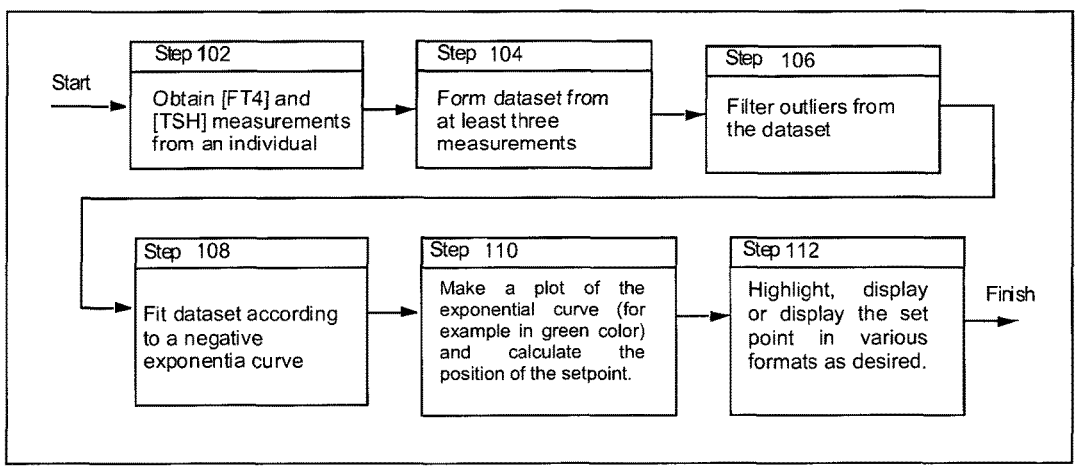
FIG. 1 is a general flow chart of the method according to an embodiment of the invention.
Figure 2:
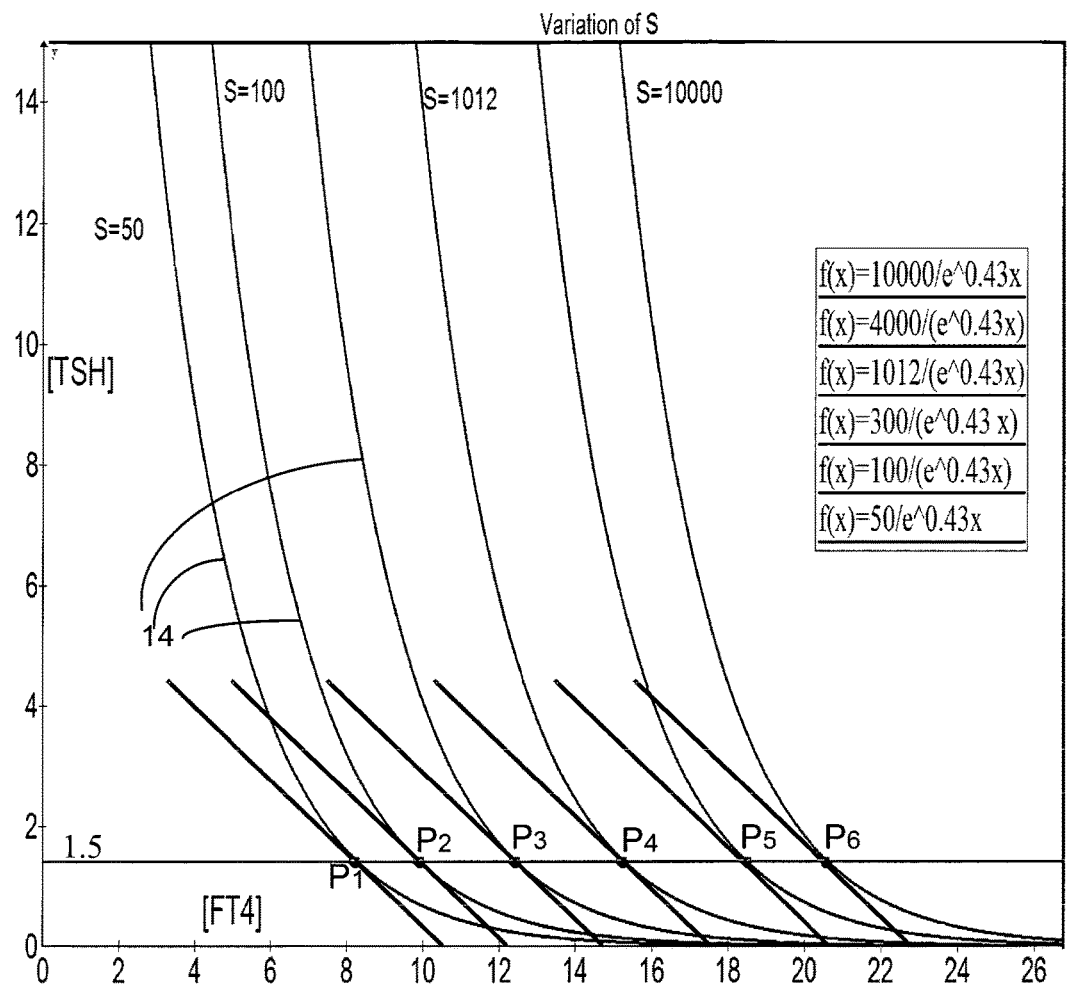
FIG. 2 illustrates examples of the HP (Hypothalamic-Pituitary) characteristic having the values of S varying between 50 to 10000 and φ at a constant value of 0.43 shifting the HP characteristic horizontally along the [FT4] axis.
Figure 3:
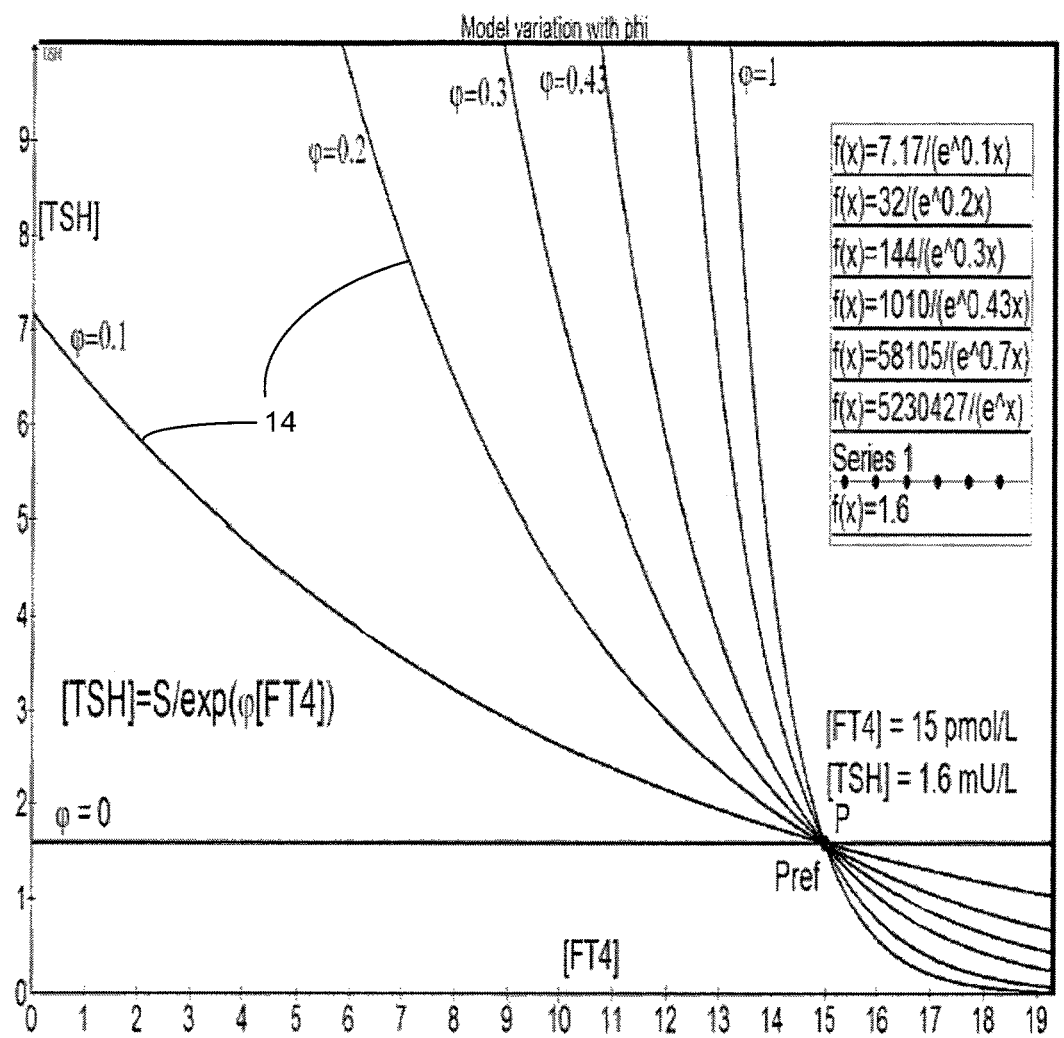
FIG. 3 depicts the theoretical range of values that φ can possibly assume under most clinical circumstances and illustrate the rotational effects when φ is changed.

FIG. 2 and FIG. 3 illustrate examples of the variation of the factor S, a linear component of the thyrotropic system, which is related to the [FT4] range; and the variation of the φ value, which is the exponential component that represents the exponential coefficient. Variation of S, with a fixed value for φ will horizontally translate the pituitary characteristic curve along the [FT4] axis where the value of the derivative for the same [TSH] will remain unchanged. Variation of φ will 'fold/unfold' the shape of the pituitary characteristic centred on a chosen set of coordinates, i.e. rotate the pituitary characteristic curve about the chosen set of coordinates.

Each homeostatic measurement comprises a value of a [TSH] reading and a corresponding [FT4] reading. To determine the S and φ parameters for the individual, at least two well distinguishable homeostatic, measurements (i.e. ([FT4]$_1$, [TSH]$_1$) and ([FT4]$_2$, [TSH]$_2$)) from the individual are obtained with a predetermined time gap in between each measurement. The measurements are performed on samples taken near the same time of the day by the same analytical measurement method and ideally applied by one and the same person whenever feasible to minimise errors that can compromise the accuracy of the model estimates.

Preferably, the individual measurements are performed in a fasting condition and separated by 6 weeks while under medical treatment for a hypothyroidism or hyperthyroidism state with the replacement hormone for [T4] leading to a state of clinical euthyroidism.

At least two homeostatic measurements could be selected from any of the known levels of thyroid stimulating hormone [TSH], with corresponding free thyoxine [FT4], free triiodothyronine [FT3], total T4, or total T3. Each homeostatic measurement may be obtained based on thyroid function test results. For the determination of the S and φ parameters to be meaningful and to facilitate the fitting of step 108, the two measurements should not be identical, but be distinguishable from each other. As a general guideline, relatively higher values of [TSH] are preferred.

Any method known for measuring homeostatic parameters would be suitable, for example, various types of chromatography, immunochemistry or other methods known to accurately measure the amount of a homeostatic expression product, as long as the same measurement method is applied by one and the same person.

Upon obtaining the at least two homeostatic measurements to form a dataset 12, the model parameters S and φ characteristic may then be determined by solving the following simultaneous equations for the model parameters S and φ:—

$$\varphi = \left(\frac{1}{[FT4]_1 - [FT4]_2}\right)\ln\left(\frac{[TSH]_2}{[TSH]_1}\right) \quad (2)$$

$$S = [TSH]_1 \exp(\varphi[FT4]_1) = [TSH]_2 \exp(\varphi[FT4]_2) \quad (3)$$

where the subscripts 1 and 2 denote the first and second homeostatic measurement respectively.

Where there is availability of additional homeostatic measurements for addition into the dataset 12, i.e. ([FT4]$_3$, [TSH]$_3$), ([FT4]$_4$, [TSH]$_4$) . . . etc. it is possible to further fine-tune the value of the parameters, S and φ by iterating the same calculation procedure between the additional homeostatic measurements and the original two measurements (provided that the thyroid function test results are not repeatedly identical). Such calculation procedure is available in many common curve fitting tools (i.e. interpolation, smoothing or extrapolation techniques etc.)

Notably, the parameters φ and S are inter-related accordingly for any [FT4]-[TSH] coordinate on the pituitary characteristic 14 according to the following mathematical formulation:—

$$\varphi = \left(\frac{1}{[FT4]}\right)\ln\left(\frac{S}{[TSH]}\right) \quad (4)$$

Once parameters S and φ are calculated, and with at least three homeostatic measurements (although two homeostatic measurements with a distinct difference are possible as long as they are trusted to be reliable) in the dataset 12, the HP characteristic in equation (1) may be curve-fitted based on the measurements in the dataset 12.

For illustration, the fitted curves (see FIGS. 4 and 5) graphically show a pronounced 'knee' region or curvature situated in the area of 'normal euthyroid reference values' of [TSH] and [FT4].

Method 10 (The derived HP characteristic) was validated with two sets of patient data from various sources. The sources are spread across different geographical locations including Singapore and Germany with different laboratory-specific reference ranges for [TSH] and [FT4], measured in mU/L and pmol/L respectively, and different genetic background of the respective populations. Each set comprises data obtained from four individuals.

Set 1 was obtained from Tan Tock Seng Hospital of Singapore (ethical approval from the National Healthcare Group Domain Specific Review Board (DSRB 'C') ethics committee, file number: C/2011/02012)—see FIG. 4; and Set 2 stems from a subpopulation of the NOMOTHETICOS trial at the Bergmannsheil University Hospitals in Bochum, NRW, Germany (UTN U1111-1122-3273, ClinicalTrials.gov: NCT01145040, approved by the ethics committee of the Ruhr University of Bochum with file number 3718-10)—see FIG. 5

Figure 4:
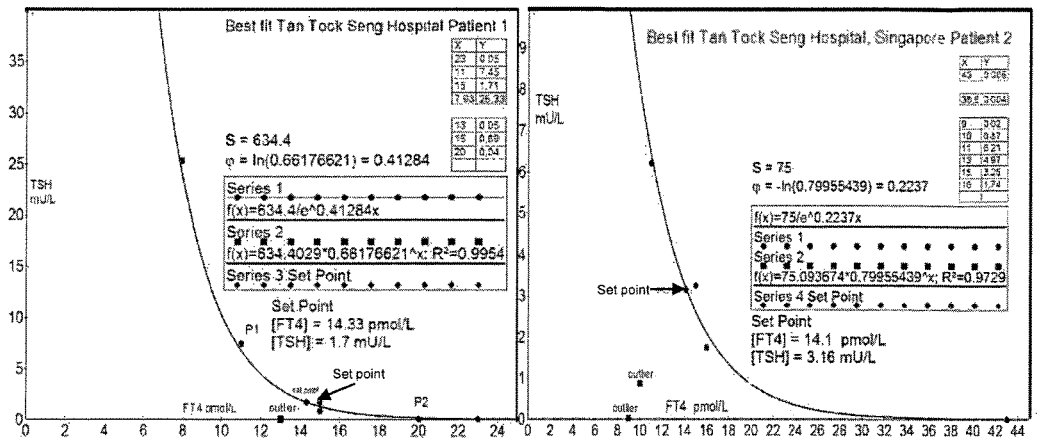
FIG. 4 shows the fitted negative exponential curves of four individuals (Tan Tock Seng Hospital of Singapore)
Figure 4:
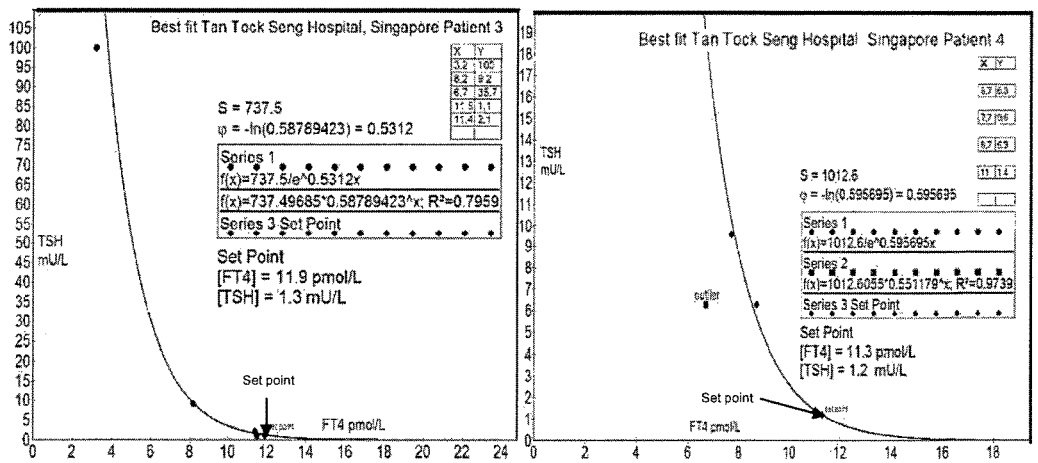
Figure 5:
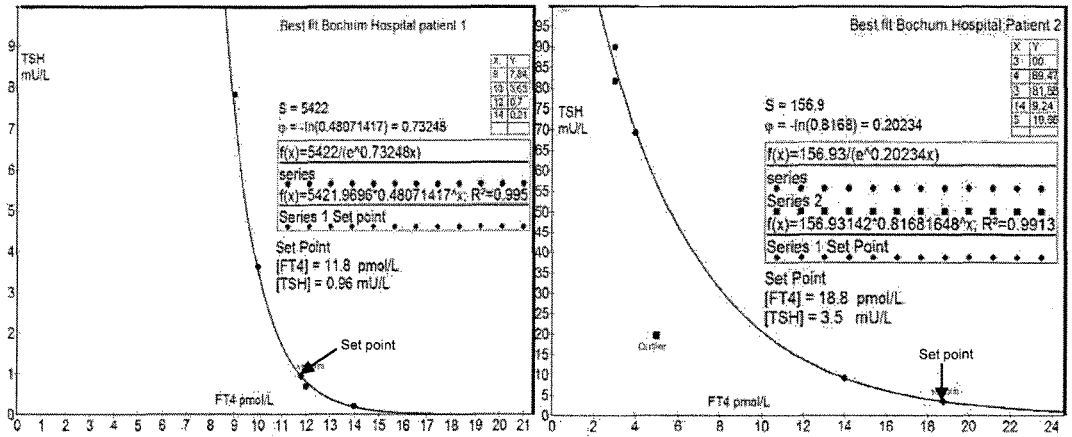
FIG. 5 depicts the fitted negative exponential curves of four individuals (Bergmansheil University Hospitals Bochum)
Figure 5:
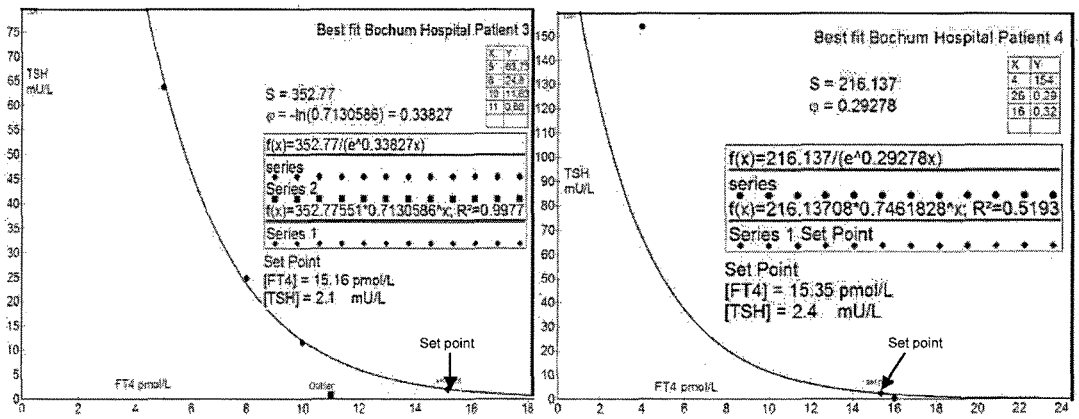

From FIGS. 4 and 5, the calculated curves from the dataset 12 of twelve different individuals show an excellent goodness-of-fit of 81%<Rsq<100% to the measured homeostatic measurements with exclusion of the outliers.

As a confirmation that the HP characteristic curve must always be deduced from individual patients and cannot simply be predicted by pre-defining the structural parameters S and φ based on current practice; a simulation analysis on the model, such as Monte Carlo simulation was performed using stochastic values of [FT4] and [TSH] within the sample space defined by all possible outcomes found in the population ranges according to a log normal distribution. In the Monte Carlo simulation, the parameters S and φ are fixed or pre-set.

Based on Monte Carlo simulation:—under noise-free ideal circumstances, when the conditions that S=300 and φ=0.5, both parameters being pre-set are prescribed, the adjusted R-squared varied from 0.4071 to 0.5017 and the F-statistic is highly significant, with estimated mean S=300 and mean φ=0.5 associated with infinitesimally small standard deviations for both estimated parameters. However, when some noise is introduced (to simulate the real life scenario), the adjusted R-squared drops to almost zero, and estimated S and φ deviating far-off, with the standard deviation of φ being relatively high. It is noted that the parameters S and φ cannot be back inferred even with little noise in the data.

The unique and divergent S and φ values as seen in the eight patients (illustrated in FIG. 4 and FIG. 5) illustrates that every individual has a unique set point. This is supported by the fact that the Monte Carlo simulation results described above is unable to use a single equation with pre-determined S and φ (i.e. S=300 and φ=0.5) to predict [FT4] and [TSH]; hence accurately lends support to the conclusion that the S and φ parameters are unique across individuals. In addition to the inter-individual variations in [FT4] and [TSH], other factors which Monte Carlo simulation is unable to address include:—the high propensity of amplification of a series of minor variability in [FT4] and [TSH] related to diurnal variations, laboratory errors, differing coefficient of variations of different laboratory assays and other sources of physiological and analytical 'noise' introduced into the HPT axis system.

The results support the notion that the parameters S and φ must always be retrospectively calculated from real patients' [TSH] and [FT4] dataset in the procedure as illustrated by the patients' HP graphs.

The obtained HP characteristic curve 14 of the individual is used to derive the physiological homeostatic operating set point 16 of the individual. This may also be referred to as the true euthyroid set point, i.e. the optimal combination of thyroid-stimulating hormone [TSH] level in milliunits per liter (mU/L) and the corresponding free thyroxin [FT4] level in picomoles per liter (pmol/L) in the individual.

Figure 6:
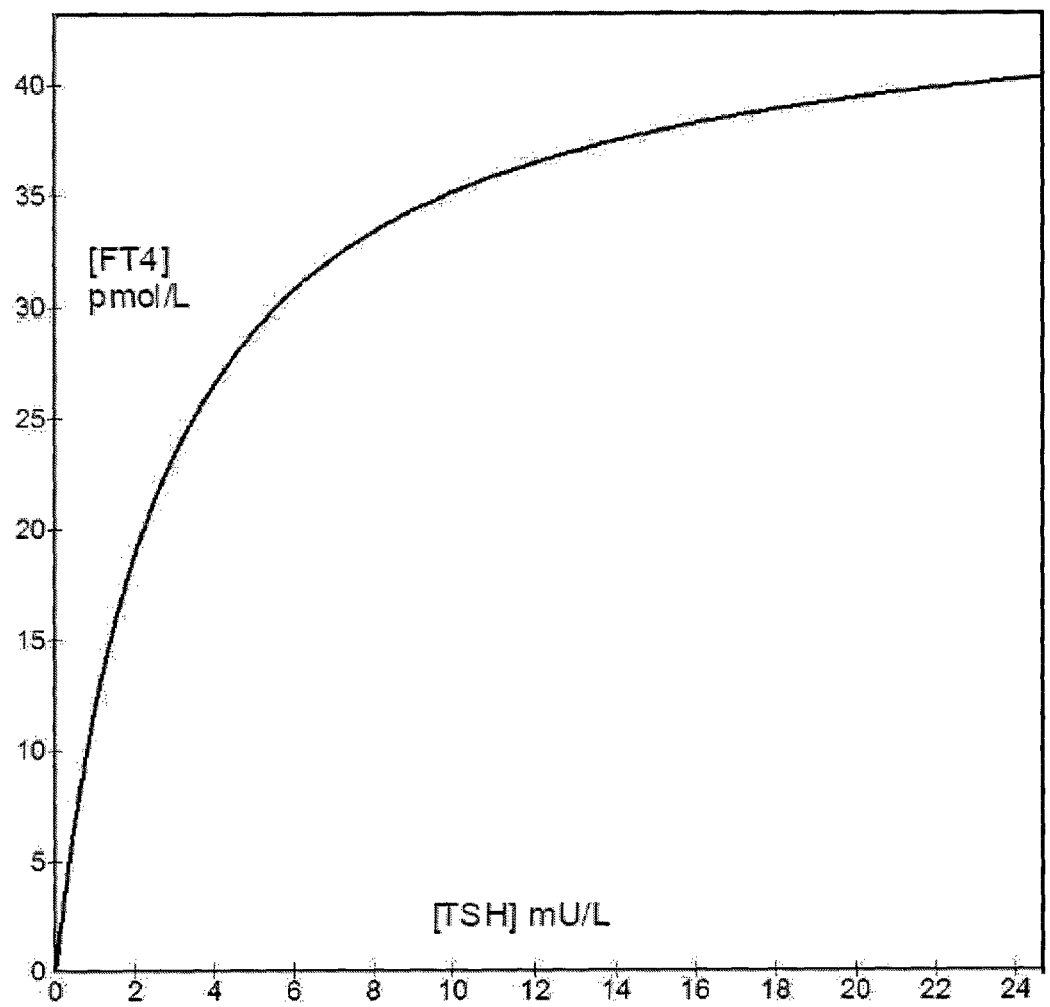
FIG. 6 shows the thyroid transfer characteristic, [FT4] as a function of [TSH].

In support of the uniqueness theory of the physiological homeostatic operating set point 16, the thyroid transfer characteristic (shown in FIG. 6), which relates to the secretion of [FT4] by the thyroid with [TSH] as an input according to the Michaelis-Menten-Hill kinetics in the form of equation (5) below is used:—

$$[FT4] = \frac{K[TSH]}{2.75 + [TSH]} \quad (5)$$

The Michaelis-Menten kinetics is adopted as they are well founded in physiological and biochemical grounds. The parameter K corresponds to different thyroid secretory capacities derived from the calculated set point.

The thyroid has a slave function and forms an additional function block in the normal (HP) thyroid feedback loop. This implies that the thyroid itself has no autonomous control about the secretion of demanded [T4] and the resulting [FT4]. The final [FT4] secretion will be determined by the HP [FT4] discriminating function and the incorporated set point criterion for [FT4] as embedded in the hypothalamus pituitary (HP) unit. The secretion of [FT4] is thus determined by the HP set point and the thyroid secretion curves will be derived from that data.

Figure 7:
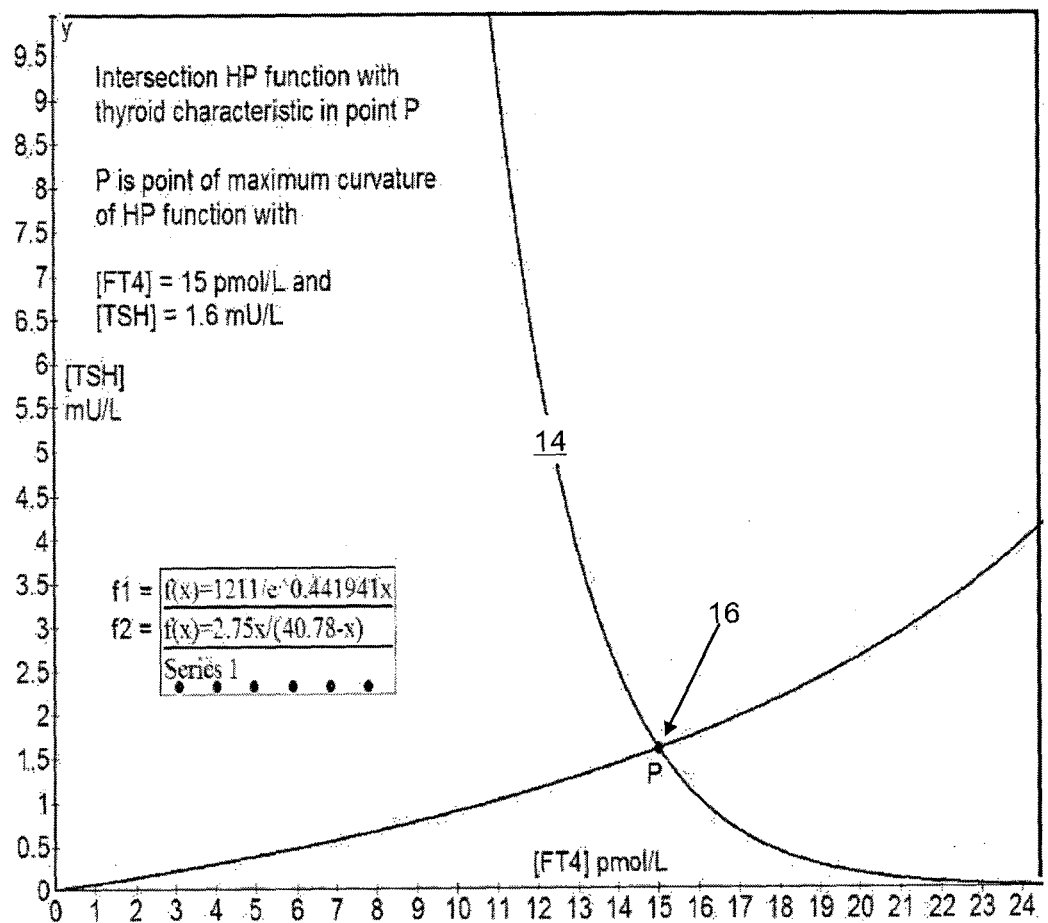
FIG. 7 illustrates an intersection of the thyroid and pituitary curves at point P locating the set point of an individual.
Figure 8:
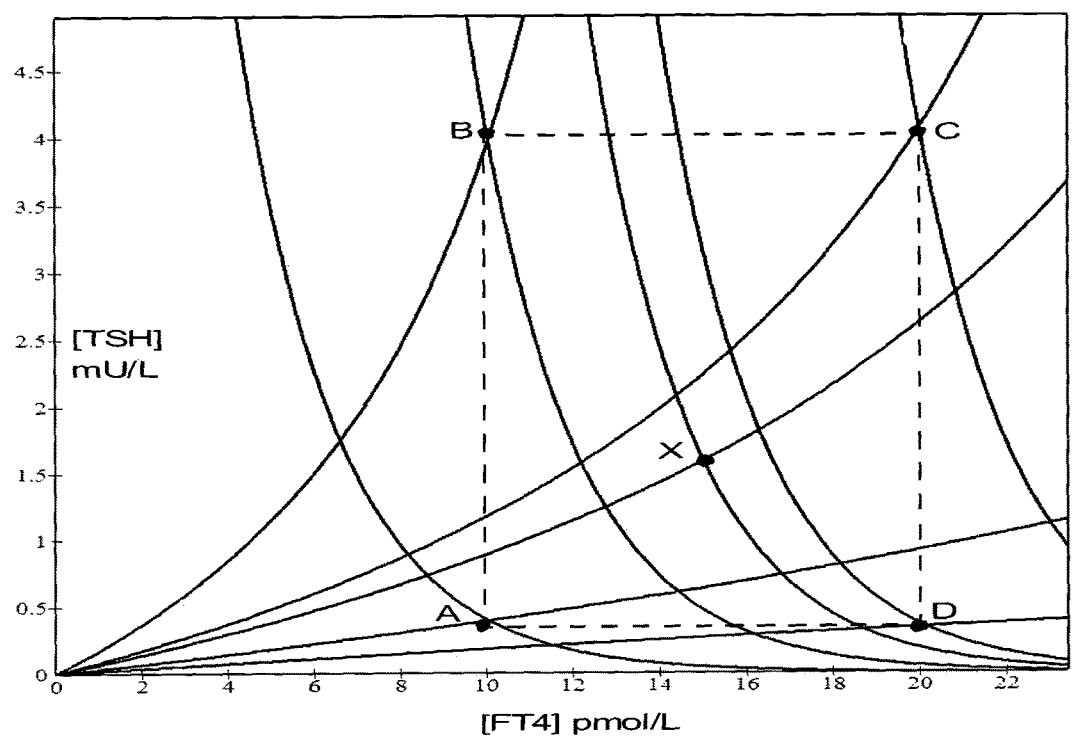
FIG. 8 illustrates five different inverted characteristics of the thyroid starting in the origin (0,0) intersecting with five characteristics of the HP resulting in the intersection points A, B, C, and D defining the reference 'normal' area as indicated by the dashed lines forming a rectangle. Point X represents the median values of [FT4]=15 pmol/L and [TSH]=1.6 mU/L found in a healthy euthyroid individual.

Based on the Michaelis-Menten kinetics, the homeostatic operating set point 16 of the individual is determined to correspond to the intersection between HP curve generated by equation (5) (See FIG. 7) and the pituitary function 14. This is another way of arriving at the unique homeostatic operating set point 16 of the individual.

Upon obtaining the fitted curve 14, the set point of the individual in the HPT feedback loop corresponds to the point on the HP function where the sensitivity for any change around this point on the curve is maximal. This means that this point of optimal sensitivity can be found in the point of maximal curvature of the HP curve of equation (1). Hence, the HP unit detects deviations of the [FT4] concentration (after its local de-iodination to [FT3]) as a positive or a negative difference compared with the location on the curve with the highest curvature—i.e. curvature gradient detection. Such a notion is consistent with biological concepts as will be explained below.

This point of maximized curvature and thus maximized sensitivity for change can be found according standard curvature theory applied to the HP function. This result in the following corresponding values of [FT4] and [TSH] for the set point:—

$$[FT4]_{SP} = \frac{\ln(S\varphi\sqrt{2})}{\varphi} \quad (6)$$

$$[TSH]_{SP} = \frac{1}{\varphi\sqrt{2}} \quad (7)$$

The set point may also be identified by calculating the first derivative of the HP function as presented in equation (8), where the value of the first derivative corresponds to or approximately −0.707

$$\frac{d[TSH]}{d[FT4]} = \frac{-1}{\sqrt{2}} = -0.707 \quad (8)$$

Figure 18:
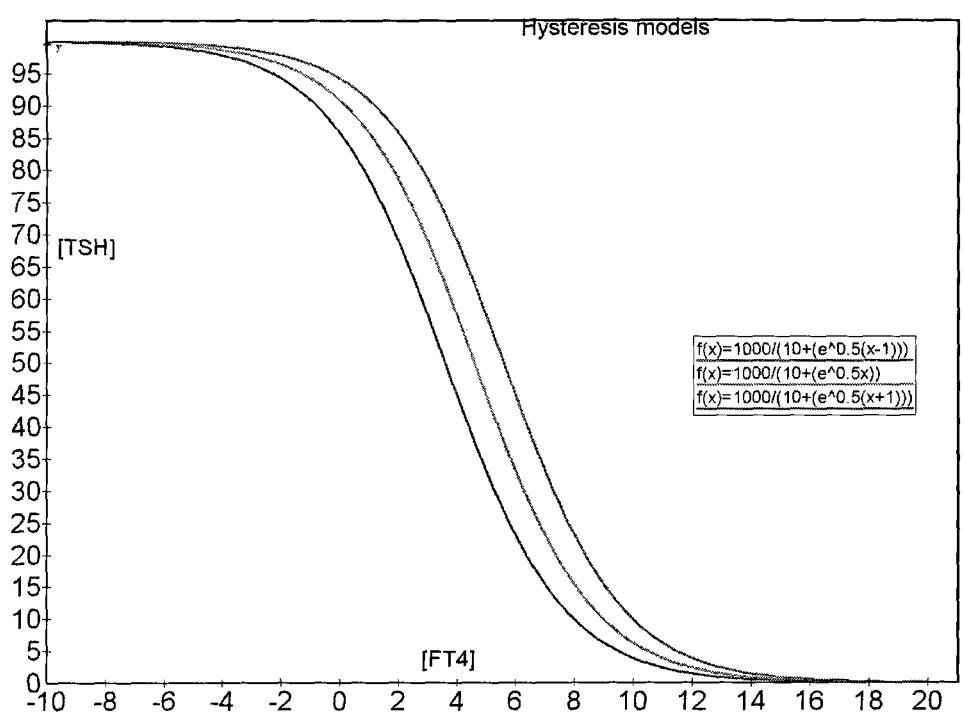
FIG. 18 illustrates the hysteresis effect based on an alternative extended model mathematically expressed as equation (10)
Figure 19:
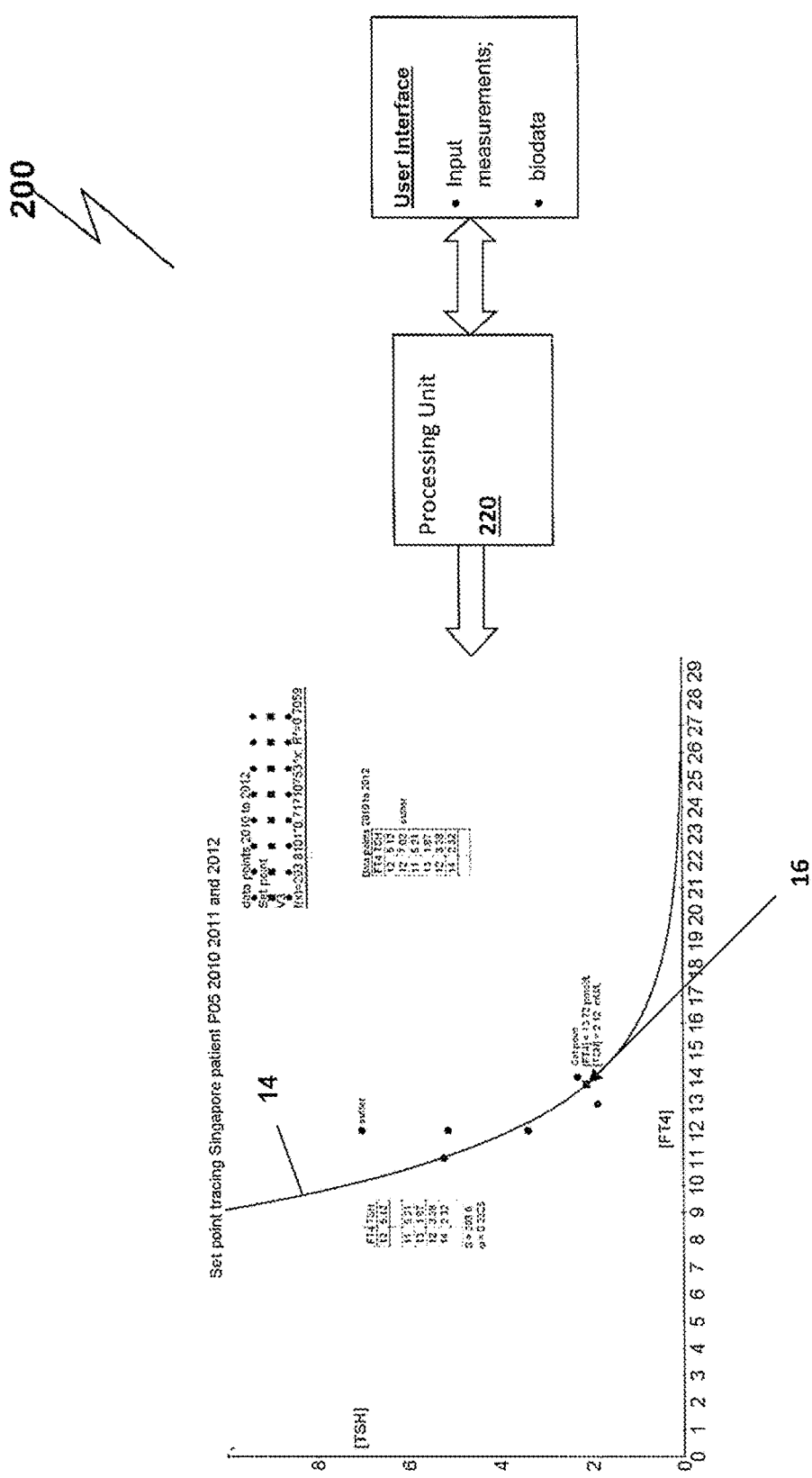
FIG. 19 illustrates the system according to another embodiment of the invention.

In accordance with another embodiment of the invention where like reference numerals designate like parts there is a system 200 for deriving a physiological homeostatic operating set point 16 of an individual as illustrated in FIG. 18.

The system 200 comprises a processing unit 220 operable to obtain a dataset 12 of predetermined number of homeostatic measurements of the individual and fit the dataset of predetermined number of homeostatic measurements according to a negative exponential decay function 14; wherein the physiological homeostatic operating set point 16 unique to the individual is identified as the point of maximum curvature on the fitted negative exponential decay function 14.

In particular, the system 200 may be used to implement the method 10 of the previous embodiment to derive the hypothalamus pituitary (HP) characteristic of the individual. The HP characteristic of the individual relates the level of thyroid-stimulating hormone [TSH] level in picomoles per liter (pmol/L) and the corresponding free thyroxin [FT4] level in milliunits per liter (mU/L) in the individual.

The system 200 may include each of the predetermined number of homeostatic measurements, which in this embodiment is the thyroid-stimulating hormone [TSH] level and the corresponding free thyroxin ([FT4]) level when the individual is fully controlled under predetermined measurement conditions. Examples of fully controlled predetermined measurement conditions include, for example under a clinical setting/environment obtained by qualified clinicians using proper measurement apparatus and techniques. The homeostatic measurements may be obtained from clinical data and/or clinical tests and trials done on the individual. Each homeostatic measurement for each individual is preferably obtained between a time interval as appropriately defined by a medical practitioner such as a clinician.

The various equations defining the negative exponential decay function 14 or HP characteristic of the individual are as laid out in equations (1) to (6) in the earlier embodiment.

The system 200 may optionally be used for a predetermined number of homeostatic measurements, each homeostatic measurement comprising the thyroid-stimulating hormone [TSH] level and the corresponding triiodothyronine [T3] level, instead of the [FT4] levels.

As described in the earlier embodiment, the dataset 12 is fitted based on non-linear regression or a non-linear method of least squares related to an exponential function.

The fitted negative exponential decay function 14 may be validated using a goodness of fit test (Rsq) comparing at least three distinctly separated sets of homeostatic measurements 12 under predetermined and controlled conditions.

The system 200 may be validated using the clinical data as described in the earlier embodiment.

Processing unit 220 may be a laptop computer, a desktop computer, mobile computer, smartphones or any other computing device capable of installing thereon software instructions that when executed by a computer causes the computer to perform the method 10 as described in the earlier embodiment. Processing unit 220 may further comprise a user interface for data input, and display of the exponential curve 14 and set point. For purpose of clarity in display, the system 200 may include some form of indicator colour, preferably a bright colour for display of the exponential curve 14 (step 110). Optionally, the set point 16 may be highlighted in flashing red (or any other colour) and the set point value may be printed (step 112). Alternatively other types of visual display/representation such as cross-hair pointers or acoustical feedback via speech synthesis may be used to highlight/feedback/announce the set point to the users.

The data input interface can be constructed as such that the input data are available in a table (e.g. Excel™ format) and are plotted in the [FT4]-[TSH] plane on a computer screen.

The data outlier filter removes [FT4]-[TSH] data pairs that are considered outside the possible range of the defined negative exponential decay function HPT model (PARX). This function can be activated to show the filtered result in the [FT4]-[TSH] plane on a computer screen.

The calculation machine or algorithm will use the filtered input data, without outliers and is activated to calculate the best possible curve fit. The algorithm is based on the method as described in the earlier embodiment, the curve fitting calculation method being based on non-linear regression or the non-linear method of least squares for obtaining parameters S, φ and obtaining the curve fitted HP characteristic.

The data output interface shows the fitting result (best fit 'R square') and is presented in a plot on the screen. Also the calculated set point may be connected to a printer for printing. (or show the calculated set point as a flashing red high light)

Hysteresis Effect

It is to be appreciated that equation (1) may be modified to take into account saturation effects or hysteresis effects to derive the physiological homeostatic operating set point of an individual. Such hysteresis effects are especially prominent for lower values of [FT4]. A modified equation (known as extended model) to account for hysteresis is mathematically expressed with the following formula:—

$$[TSH]=S/\alpha S+\exp(\varphi[FT4]) \qquad (9)$$

Wherein the parameters S and φ have the same meaning as that depicted in equation (1).

A model parameter α introduces a new degree of freedom defining the maximum [TSH] secretion from anterior pituitary under conditions of complete hypothyroidism. This represents the third model parameter α for each individual.

Under complete hypothyroidism, [FT4] is not detectable (i.e. at very low levels corresponding to near negligible levels where [FT4]≈0), and a maximum [TSH] secretion corresponds to saturation. From a control theory viewpoint, the system in saturation is a system which is 'out of control' or does not achieve stability.

The hysteresis effect is a non-linear 'memory effect' and can practically be described by the equation (9) where only the value of S changes.

Figure 15:
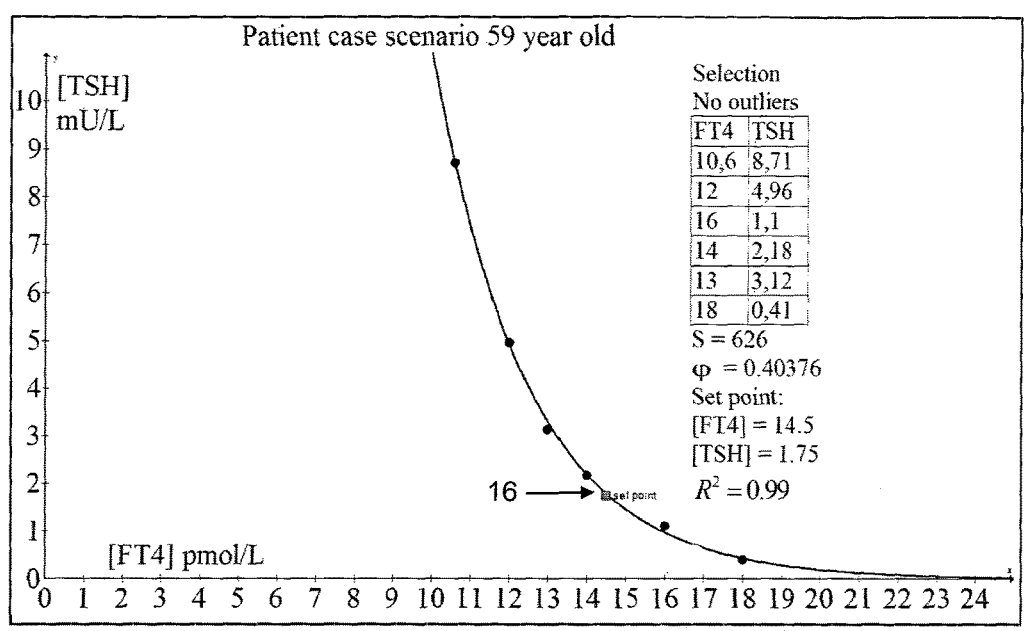
FIG. 15 is the clinical trial validation of example 6 with loop gain calculation for further validation.

Shown in FIG. 15, where the parameter α is 1/100 resulting in a maximum secretory pituitary capacity of 100 mU/L, it is shown that the hysteresis effect takes place starting in the curve 'A' with decreasing [FT4] where [TSH] tends towards an area of saturation (defined by an area where further decrease in [FT4] does not result in noticeable increase in [TSH]).

The saturation results in a physiological condition such that it will take a certain amount of increased [FT4] after which the saturation effect has been compensated and all physiological processes and conditions have been returned to the non-saturated situation and the normal physiological response can take place all be it with a shifted HP characteristic. Graphically on FIG. 15, this would mean once the saturation effect has been compensated the [FT4] values follows curve 'B' instead of curve 'A' in its return path (having an S value from 1600 to 16000. This also results in a shifted set point position, as illustrated in FIG. 16, which shows the enlarged portion of the set points.

It is also observed that when values of [FT4] are saturated at a relatively high [FT4] value such as 40 pmol/L, the return path after compensation of saturation will result in a change in S value and shifts in the set point.

Figure 16:
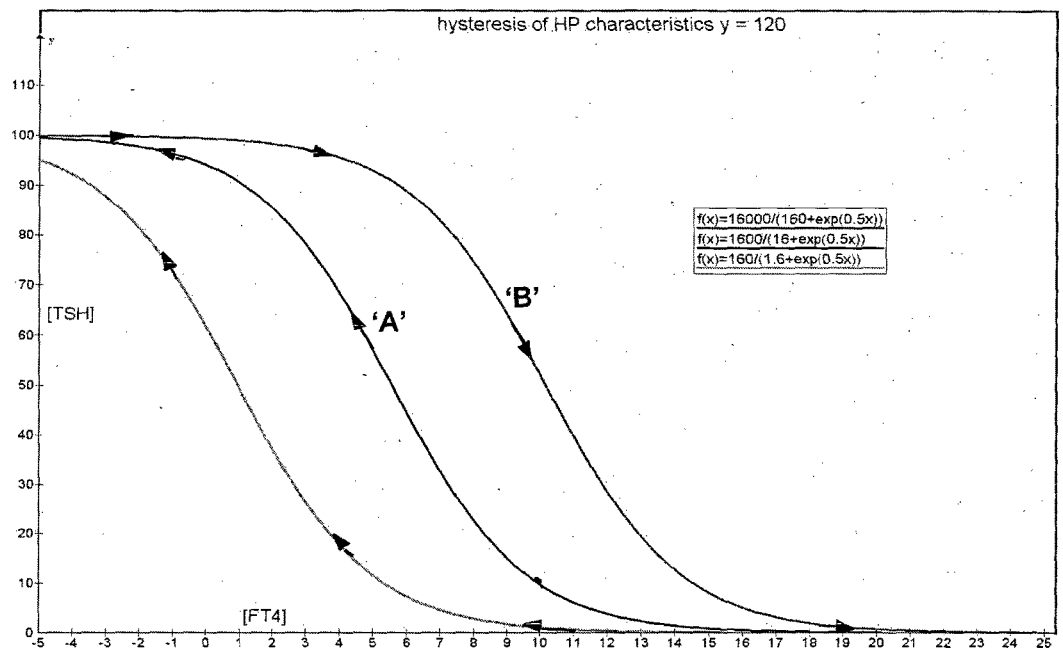
FIG. 16 illustrates the hysteresis effect based on the extended model mathematically expressed as equation (9)

FIG. 16 illustrates three curves with different S values illustrating effects of hysteresis, it is appreciated that shifts in set points compared to original set point is averaged at plus or minus 4.5 pmol/L. The derivative (i.e. gradient) for each of the set point is identical because of the unchanged exponential coefficient φ.

Practically, it is to be appreciated that average [FT4] values of the individual may be calculated to find the original set point only when hysteresis curves are available. The proposed model equation (9) may be used to work out the characterization for the maximum TSH secretion from anterior pituitary under conditions of complete hypothyroidism where [FT4] is not detectable, [TSH] has entered the saturation stage and the system is out of control as described earlier.

Equation (9) may be further modified to take into account the likelihood that the parameter S is not completely independent. The modified modelling of the hysteresis behaviour is mathematically expressed as equation (10).

$$[TSH] = \frac{S}{\alpha S + \exp(\varphi([FT4] + \varepsilon))} \qquad (10)$$

Equation (10) introduced an additional fourth exponential shift parameter E. The addition of the parameter ε provides an extra degree of modelling freedom.

The range of e can be found from $-X \leq \varepsilon < X$ where X is a real number between 0 and 10. An added criterion is that the value of X has to be smaller and in the same order as the value range for [FT4].

Figure 17:
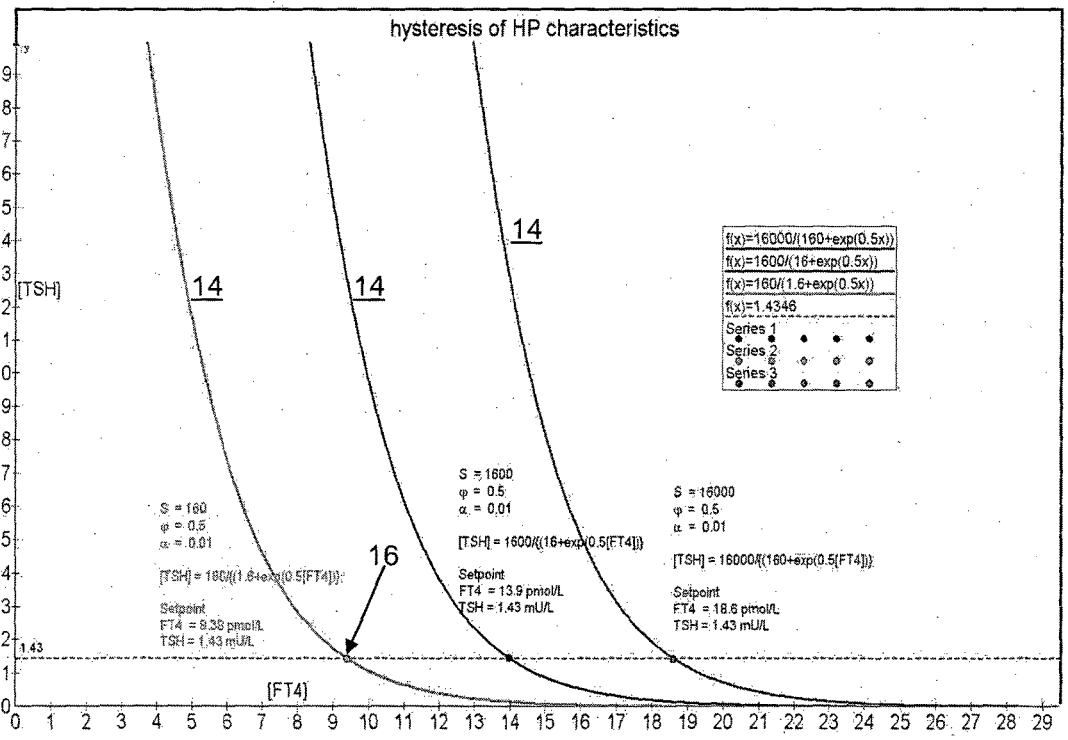
FIG. 17 illustrates the hysteresis effect with particular focus or zoom-in on set point region based on the extended model mathematically expressed in equation (9)

In the alternative modelling, the parameter S remains constant as an original model parameter of the normal HP characteristic. The effect of changes of the parameter ε is illustrated in FIG. 17 where X is 1. It is apparent that the parameter ε has the effect of shifting the complete saturated HP characteristic along the [FT4] axis without affecting the original value of S.

For the described embodiments, it is to be appreciated that each measurement for the dataset 12 may be obtained via a variety of methods, standards and essays; including (but not limited to the example as described below):—

An example of how a measurement from the dataset 12 is obtained is via measuring the amount of a homeostatic amino acid expression product with a detection reagent capable of hybridizing to the homeostatic amino acid expression product. The detection reagent may be similar to those known in the art. In a preferred embodiment the detection reagent comprises an antibody and a detectable marker. The amount of a homeostatic amino acid expression relates the level of thyroid-stimulating hormone [TSH] level in picomoles per liter (pmol/L) and the corresponding free thyroxin [FT4] level in milliunits per liter (mU/L) in the individual.

Preferably the detection antibodies to any homeostatic amino acid such as TSH or T4 would be suitable. Exemplary antibodies must be capable of hybridising to any homeostatic amino acid such as TSH or T4 by having a high specific affinity to the target homeostatic amino acid such as TSH or T4. In a preferred embodiment the antibody is capable of hybridizing to a thyroid-stimulating hormone. In another preferred embodiment the antibody is capable of hybridizing to a free thyroxin alone or in combination with a second antibody capable of hybridizing to a thyroid-stimulating hormone. Preferably, the antibody is capable of hybridizing to 90 to 95% of the target homeostatic amino acid to provide a high specific affinity to the target homeostatic amino acid. The antibodies may include polyclonal, monoclonal, and humanized, antibodies, conjugated antibodies or any antibodies known in the art suitable for detection.

Preferably, the detection reagent comprises an antibody and a detectable marker. The antibody may be to any homeostatic amino acid such as [TSH] or T4. Any detection markers known to demonstrate the amount of antibody interaction would be suitable, such as GFP, an enzyme linked colorimetric detection marker, biotin conjugates, radiolabels, stains or any other detectable markers known to work in detection of the amount of amino acid expression in cell or mammal. Detection methods may include any of those known in the art such as Western blots, dot blots, IHC, IP, FACS, ICC, Enzyme-linked immunosorbent assay (ELISA), or any other method for detecting the amount of amino acid expression in cell or mammal.

In one embodiment the system 200 may further comprise a means of obtaining a measurement from the dataset comprising a detection reagent capable of hybridizing to a homeostatic amino acid expression product and a means of detecting an interaction between the detection reagent capable of hybridizing to a homeostatic amino acid expression product and the homeostatic amino acid expression product. This is measured by a concentration of the homeostatic amino acid expression product in the blood. The reagent may be an antibody as described above and the detection means may be via ELISA detection.

Therapeutic Adjustment

An individual having homeostatic measurements at or near the calculated physiological homeostatic operating set point unique to the individual is deemed to be in a euthyroid state. Hence, once the physiological homeostatic operating set point unique to the individual is calculated preferably a therapeutically effective amount of a compound able to adjust the homeostatic measurements of the individual to the calculated physiological homeostatic operating set point unique to the individual is administered to the individual. In one embodiment the therapeutically effective amount of a compound comprises thyroxin. Alternatively, an active iodothyronine, iodothyroacetic acid or combinations of thyroxin and other iodothyronines or iodothyroacetic acids may be administered. Other compounds such as antithyroid drugs, sodium perchlorate or radioactive iodine-131 may also be administered to adjust the individual's homeostatic measurements to the calculated physiological homeostatic operating set point unique to the individual.

In one embodiment the system 200 further comprises a means of adjusting the homeostatic measurements of the individual to the calculated physiological homeostatic operating set point unique to the individual using a therapeutically effective amount of a compound able to adjust the homeostatic measurements of the individual. The therapeutically effective amount of a compound able to adjust the homeostatic measurements of the individual is as described above.

Physiological Theory of the Homeostasis Process.

Figure 9:
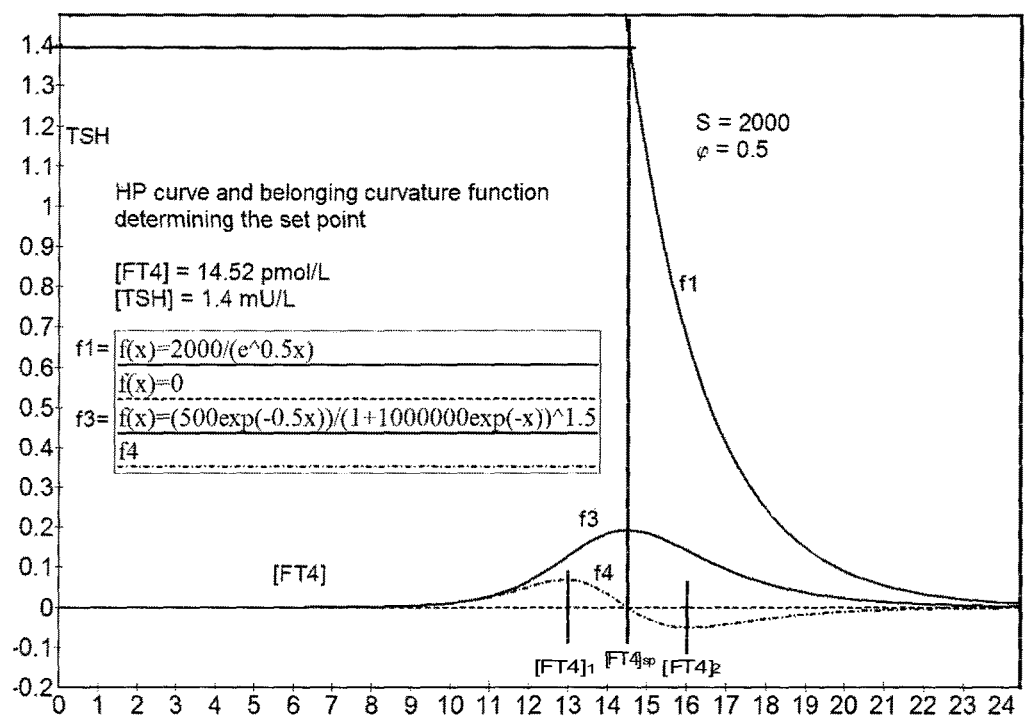
FIG. 9 illustrates the physiological mechanism explaining the stabilization process of the homeostatic set point.
Figure 10:
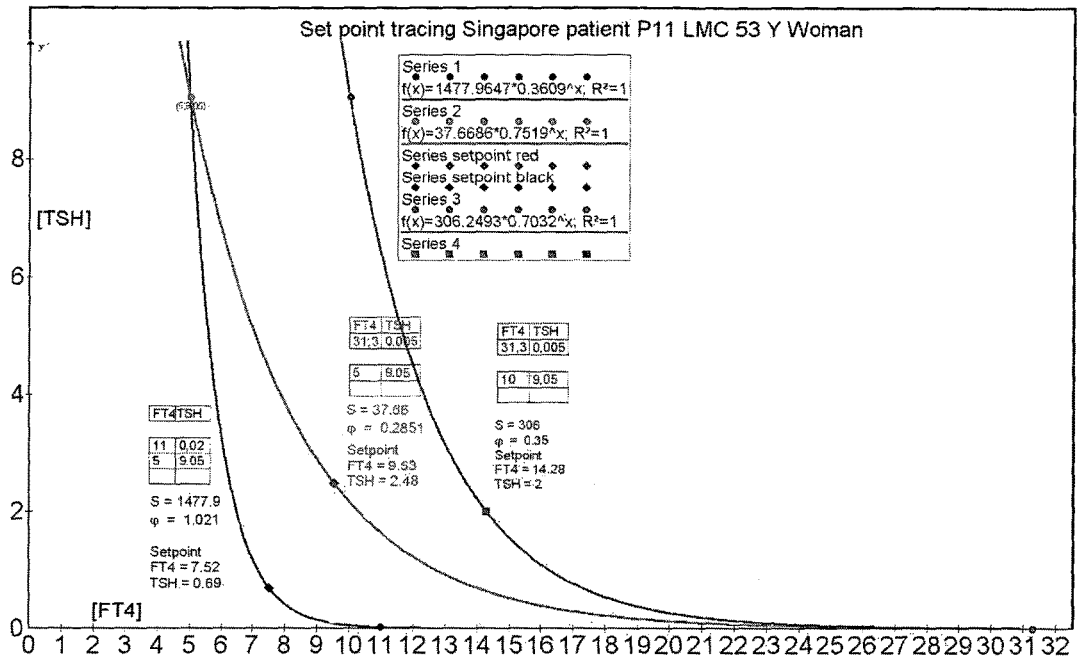
FIG. 10 shows the clinical trial validation of example 1.

The functions of the HP (curve f1), the function for the curvature of f1 (curve f3) and the derivative of the curvature function f4, are shown in one graph as depicted in FIG. 9.

The curvature function f3 is mathematically expressed as:—

$$f3 = K_r = \frac{\varphi^2 S \exp(-\varphi x)}{(1 + \varphi^2 S^2 \exp(-2\varphi x))^{1.5}} \quad (11)$$

and $K_r$ denotes the point of maximum curvature.

The theory for the maintenance of homeostasis around the set point is the following.

The second derivative of $K_r$ is mathematically expressed as:—

$$\frac{d^2 K_r}{d[FT4]^2} = 0 \quad (12)$$

As illustrated in FIG. 9, two extremes on f4 resulting in $[FT4]_1$ and $[FT4]_2$ are found. The HP unit in the brain measures the gradient and the concentration of [FT4] and uses the criterion [FT4] together with the positive gradient of [FT4] to disable the thyroid hormone production. When the thyroid production is disabled, the flywheel effect of the T4 and T3 production process will result in the following.

The [FT4] concentration will pass $[FT4]_2$, after that, the gradient becomes zero and will then be negative as a result of decreasing [FT4]. Then [FT4] will pass $[FT4]_2$ again, together with the negative gradient of [FT4] and the decision concentration of $[FT4]_2$, the thyroid receives an enabling signal from the HP unit. Just like a switching regulator with hysteresis found in thermostats.

Accordingly, by plotting both the graphs of the curvature function and its first derivative (which measures the rate of change of curvature with respect to [FT4] concentrations) with the superimposed [TSH]-[FT4] curve, it can be appreciated that fluctuations of [FT4] around the calculated set point will behave such that [FT4] levels on either sides of the set point tend to oscillate and fall towards the set point to achieve homeostatic equilibrium. In terms of physiology, this necessarily means that the hypothalamus-pituitary complex must necessarily detect both the [FT4] concentration and its rate of change (i.e. positive vs. negative 'gradient') to either disable or enable the thyroid to secrete thyroid hormones akin to a switching thermostat temperature control regulator. This property of the set point as determined has been shown to be stable using stability analysis of systems theory. The result is that the set point so calculated is analogous to stable equilibrium of a ball perched at the bottom of a valley or a conical cup, such that any displacement of the ball away from the lowest point of the valley or cup (i.e. set point) will lead to the ball rolling back towards it by virtue of the law of conservation of energy.

Stability of the Derived Set Point Based on Loop Gain Calculation $G_L$

In addition to a model for deriving the unique homeostatic operating set point of each individual as described in the earlier embodiments, the inventors had adopted an investigation based on the concept of loop gain as mathematically expressed in equation (13).

$$G_L = \frac{A\varphi}{e} \quad (13)$$

with e=2.7182 being the exponential constant; the parameter A is obtained from an enzyme kinetic model, which is known and may be considered as an alternative model to the MM kinetics model mathematically expressed in equation (5). The enzyme kinetic model is mathematically expressed as follows:—

$$[FT4] = A\{1 - \exp(-\alpha[TSH])\} \quad (14)$$

$$\text{and } A = \frac{[FT4]_{setpoint}}{0.632} \quad (15)$$

When the optimal [FT4] of an individual is obtained, the corresponding A and φ the rotational (exponential) parameter is substituted in equation (13) and (15). As an optional added criterion to the earlier described embodiments, in order for the set-point to be accepted, the value of $G_L$ (i.e. the loop gain) must be greater than 1 to indicate stability.

Proof of the Set Point Validity Using Control Theory with Michaelis Menten Thyroid Model The inventors have adopted an independent proof of the validity of the derived homeostatic operating set point described in the earlier embodiments based on control theory principles. In particular, the inventors adopted a control system model where the hypothalamus pituitary system is modeled as a controller unit (referred to as 'HP controller unit'); and the thyroid interacts with each other under optimal conditions.

The dynamic transfer functions of the HP and thyroid under such optimal conditions may be written as the first derivatives of the respective functions $$G_{HP} = \frac{d[S\exp(-\varphi[FT4])]}{d[FT4]} = -\varphi S\exp(-\varphi[FT4]) = -\varphi[TSH] \quad (16)$$

The thyroid function may be written in the parameterized form of equation (5), expressed as equation (17)

$$[FT4] = \frac{K[TSH]}{a+[TSH]} \quad (17)$$

Substituting [FT4] with the above equation, the transfer function $G_T = d[FT4]/d[TSH]$ may be re-written as:—

$$G_T = \frac{d\left[\frac{K[TSH]}{a+[TSH]}\right]}{d[TSH]} = \frac{K(a+[TSH]) - K[TSH]}{(a+[TSH])^2} = \frac{aK}{(a+[TSH])^2} \quad (18)$$

The loop gain is defined as the absolute value of the product of the dynamic transfer functions of HP and thyroid.

$$G_L = |G_{HP} G_T| = \left|\frac{aK\varphi[TSH]}{(a+[TSH])^2}\right| \quad (19)$$

$G_L$ may thus be expressed as a sole function of [TSH].

The thyroid and HP controller unit form a negative feedback closed loop control system, maintaining a narrow area of the set point defined value of [FT4].

This control is maintained under the condition that the value of the loop gain is at maximum. This maximum is calculated from the first derivative of $G_L$ and investigated under the condition where the first derivative of $G_L$ is equal to zero (i.e. an optimal point).

$$\frac{dG_L}{d[TSH]} = 0 \quad (20)$$

This results in $$\frac{dG_L}{d[TSH]} = \frac{K\varphi(a^2 - a[TSH])}{(a+[TSH])^3} \quad (21)$$

The extreme value of the loop gain $G_L$ is then found according $$a^2 - a[TSH] = 0 \quad (22)$$

or $$[TSH] = a \quad (23)$$

then $$G_L = \frac{a^2 K\varphi}{(2a)^2} = \frac{K\varphi}{4} \quad (24)$$

From equation (23) we see that this loop gain maximum of $G_L$, when [TSH]=a, is only dependent of the MM model parameter X' and the HP model parameter 'φ'.

When the value of [TSH] of the set point is known, we can establish the belonging MM model parameter 'a' as follows:

$$a = [TSH]_{setpoint} \quad (25)$$

The final MM thyroid model fulfilling the demand of maximum loop gain in the set point is then:

$$[FT4]_{setpoint} = \frac{K[TSH]_{setpoint}}{[TSH]_{setpoint} + [TSH]_{setpoint}} = \frac{K}{2} \quad (26)$$

or $$K = 2[FT4]_{setpoint} \quad (27)$$

The thyroid model parameters are fundamentally dependent on the values of the set point coordinates dictated by the properties of the HP.

This proof shows the independent intersection conditions of the HP and thyroid characteristics in the set point.

CLINICAL EXAMPLES

Examples of clinical application of the hypothalamic-pituitary-thyroid (HPT) axis set point theory for six individuals (patients) are as follows. Each patient may belong to one or more of the categories as listed below:—
(1) patients with a prior record of their previously normal euthyroid [FT4]-[TSH] data long before the onset of their thyroid dysfunction
(2) following up prospectively euthyroid people positive for thyroid autoimmune markers over years until their thyroid disease manifests, upon which the subsequent [FT4]-[TSH] curves plotted with set points calculated can be matched against the originally normal [FT4]-[TSH]
(3) search existing literature on epidemiology with published laboratory data documenting the natural history of those who are screened positive for thyroid autoimmune markers associated with an euthyroid state initially and who then subsequently develop thyroid disease.
(4) people with total thyroidectomy (e.g. thyroid cancer, massive multinodular goiter, etc) who then require life-long L-T4; their original pre-operative [FT4]-[TSH] levels would be their original set points
(5) euthyroid people with confirmed normal [FT4]-[TSH] (i.e. true set point) who are transiently induced to hypothyroidism (thionamides) and hyperthyroidism (i.e. L-thyroxin or L-T3) in order to generate their unique [TSH]-[FT4] curves.
(6) euthyroid people with a record of normal [FT4]/[TSH] (i.e. original set point) who received radiation therapy for head and neck who then developed hypothyroidism requiring LT4 replacement (7) patients with Graves' disease (without any prior normal TFT result to serve as set point reference) but who successfully achieved a sustained clinical remission with antithyroid drug and remained biochemically and clinically euthyroid without any drug therapy. [FT4]/[TSH] values during the remission may be considered as the original set point (8) unusual patients with "euthyroid Graves' disease", whose [FT4]/[TSH] data pairs are always consistently within the normal ranges could possibly be considered as their euthyroid set points. These patients are euthyroid due to a equimolar mixture of [TSH] receptor stimulating and blocking autoantibodies such that their reaction stoichiometric ratio at the level of the [TSH] receptors leads to neither a hypothyroid nor hyperthyroid state despite presence of TRAbs in their blood. However, over time, some of these euthyroid GD patients may develop thyrotoxicosis if their stimulating antibodies exceed blocking antibodies; or conversely, they may develop hypothyroidism if their blocking antibodies exceed their stimulating antibodies functional concentrations.

Example 1

53 yr/Female

Person has 3 sets of normal thyroid function tests done pre-lithium treatment which could represent her euthyroid set point PRIOR to the development of her Graves' disease.

|  | Day: | | | | | |
|---|---|---|---|---|---|---|
|  | 0 | 53 | 86 | 125 | 210 | 269 |
| FT4: | 53.3 | 12.5 | 31.3 | 11 | 5 | 10 |
| TSH: | <0.01 | <0.01 | 0.005 | 0.02 | 9.05 | 0.12 |
| Rx: | CMZ 20 | CMZ 10 | CMZ 30 | CMZ 10 | LT4 50 | LT4 50 |

Her thyroid was ablated with 18 mCi of radioiodine-131, following which carbimazole (CMZ) could be stopped while L-T4 was started at 50 mcg daily. Although she was compliant to LT4, she admitted to being chaotic with the timing of LT4. As such, the medical practitioner continued with the same dose but told her she must only take it at about the same time each morning before breakfast. She has some cold intolerance when FT4 was 5 with TSH at 9.05. But on day 125, she said she does not have any more cold intolerance but has increased bowel movement frequency with soft stools and diarrhoea, indicating that the latest set of TFT on day 269 must be significantly more thyrotoxic than her normal euthyroid set point.

By the method 10 and applying the most appropriate values of S and φ, the predicted set point is:

[FT4]=14.28 pmol/L
[TSH]=2.00 mU/L

The original 3 sets of TFTs obtained in the years as a pre-lithium screening before she was treated with lithium carbonate for her bipolar disorder which ultimately triggered her hyperthyroidism were:

| Day: | 0 | 680 | 1047 |
|---|---|---|---|
| [FT4]: | 14.6 | 13.9 | 13.9 |
| [TSH]: | 1.72 | 2.98 | 2.34 |

These hormone levels represented her euthyroid set points and were notably very close to the predicted values above. Hence, her L-thyroxin doses and target for [FT4] and [TSH] may be adjusted.

Example 2

52 yr/Female

Case of stage I medullary thyroid carcinoma diagnosed at day 0. Total thyroidectomy was performed at day 30, following which patient required lifelong L-thyroxin replacement.

Patient had a documented set of normal thyroid function test pre-operatively at −258 days when she was totally euthyroid, which meant her original pre-operative [FT4]-[TSH] values must necessarily be the 'true HPT axis set point'. Her post-op TFT values (as L-thyroxin doses are adjusted) are:

[FT4] (pmol/L): 9, 12, 15, 17, 19, 21
[TSH] (mU/L) 20.56, 13.24, 2.15, 1.09, 0.05, 0.01

Figure 11:
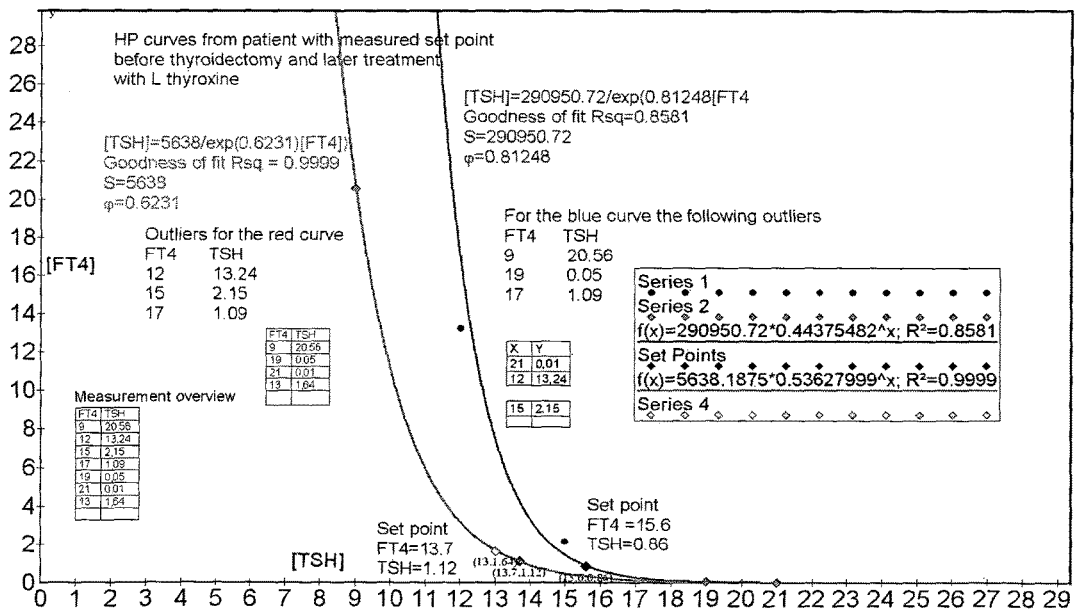
FIG. 11 is the clinical trial validation of example 2.

Reconstruction HP curves based on measured set points the Patient shown in FIG. 11

Comment on the Set Point Reconstruction

Of the 2 possible HP curves as plotted, the curve on the left has the better goodness-of-fit as evidenced by the very high R-squared value of 0.9999.

The predicted HPT axis set point was:

[FT4]=13.7 pmol/L & [TSH]=1.12 mU/L.

The patient's actual HPT set point was:

[FT4]=13.0 pmol/L & TSH=1.64 mIU/L.

Considering that both data pairs are very close in terms of their values and their order of magnitude, the math model in this example performed reasonably well.

Example 3

63 yr/Male

Presented to the ophthalmologist with diplopia (double vision). Found to have extraocular muscle features on CT scans of his orbits consistent with Graves' ophthalmopathy, but his initial thyroid function test (TFT) was surprisingly normal. This is thus a classic example of "euthyroid Graves' disease", which is due to the result of a mixture of TSH receptor stimulating and blocking polyclonal autoantibodies. The end result is euthyroidism with normal [FT4] and [TSH] levels. This may arguably be considered as the patient's original set point as many doctors and even endocrinologists may argue. The weakness of this argument is that his original HPT set point might well be somewhat different at a time when such TSH receptor antibodies were non-existent in his system, and the euthyroid TFTs are merely a reflection of his "new equilibrium or homeostatic point" emerging from the 'tug-of-war' between the 2 kinds of polyclonal antibodies.

To demonstrate that a calculated set point by the method 10 as described would prove superior to the range assumed by the majority of clinicians to be ideal, the following data speak for themselves. One such TFT obtained at the initial consultation (day 0) while he was still clinically euthyroid showed:

[FT4]=9 pmol/L (normal range: 8 to 21)

[TSH]=1.5 mIU/L (normal range: 0.4 to 5.6)

During the course of follow-up, he gradually developed hypothyroid Graves' disease due to predominant blocking antibodies "winning" and overwhelming over his TSH receptor stimulating antibodies and showed symptoms of hypothyroidism (very lethargic and sleepy) a year later which was confirmed biochemically. He was thus started on L-thyroxin from day 456 at 25 mcg daily, and escalated to 50 mcg daily from day 715. Another 2 dose increments were made on day 1085 and day 1337 (75 mcg L-T4 daily) which led to euthyroidism and resolution of all his hypothyroid symptoms.

| Year 1 | | | |
|---|---|---|---|
| Day: | 352 | 456 | 574 |
| FT4 | 8 | 8 | 10 |
| TSH | 5.55 | 6.78 | 5.35 |

| Year 2 | | |
|---|---|---|
| Day: | 715 | 862 |
| FT4 | 8 | 12 |
| TSH | 6.21 | 5.02 |

| Year 3 | | | |
|---|---|---|---|
| Day: | 1051 | 1085 | 1337 (still very sleepy in the afternoons) |
| FT4 | 12 | 12 | 11 |
| TSH | 5.12 | 7.02 | 5.21 |

| Year 4 | | |
|---|---|---|
| Day: | 1499 | 1681 |
| FT4 | 13 | 12 |
| TSH | 1.87 | 3.38 |

| Year 5 | |
|---|---|
| Day: | 1898 (he feels at his peak of health!) |
| FT4 | 14 |
| TSH | 2.32 |

Figure 12A:
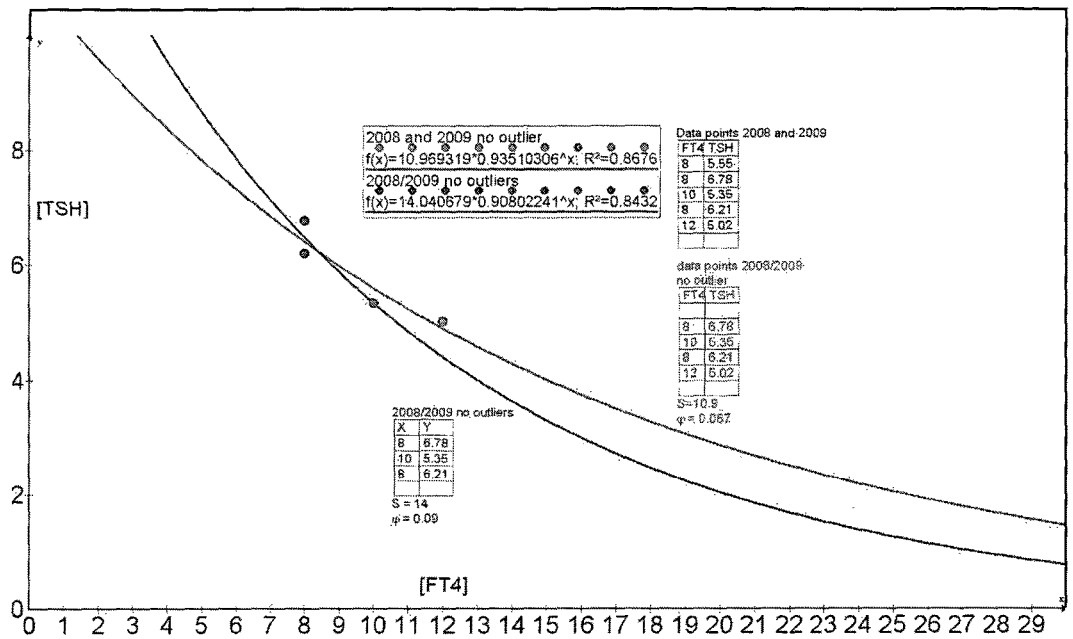
FIG. 12a and FIG. 12b are the clinical trial validation of example 3.

Data analysis over the period according to the method is shown in FIG. 12a.

The results from FIG. 12a show the state of a system in distress. There is no serious estimation of a possible set point position. This situation changes as shown in FIG. 12b, showing the Data analysis over the period from the third to fifth years of treatment.

Figure 12B:
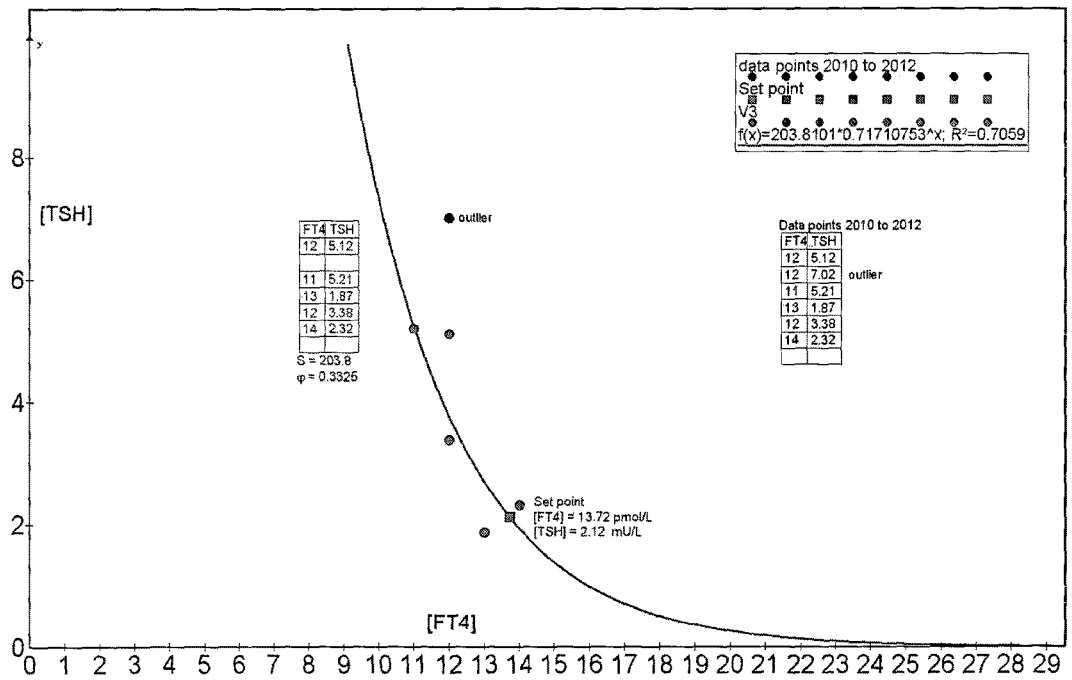

From FIG. 12b, it is clear that the predicted set point based on method 10 is found at $[FT4]_{SP}$=13.72 pmol/L $[TSH]_{SP}$=2.12 mU/L This computed set point makes perfect clinical sense, since he was still feeling tired and relatively hypothyroid when [FT4]=11 & TSH=5.21, but he feels a whole lot more energetic when [FT4]=14 and TSH=2.32.

The fact that his TFT at his peak and pink of health (i.e. [FT4]=14, TSH=2.32) being almost a perfect match to the computed set point values ([FT4]=13.72, TSH=2.12) indicate that this is the patient's original HPT axis set point rather than the initial value obtained. This could thus represent another example where a patient actually feels subjectively better when his TFTs lie at a certain point which corresponds pretty close to what our model has yielded to be the supposed set point. The model is therefore able to yield a correct set point while it would likely take clinicians much longer using traditional "guesswork" to elucidate what his set point should be, not to mention that they may even be misled by his initial TFT taken prior to onset of hypothyroidism as his "true" set point which would have been a mistake.

Example 4

The patient is a middle-aged gentleman previously repeatedly tested to be biochemically euthyroid (pre-radiotherapy). He then developed nasopharyngeal cancer (NPC) with cervical (neck) lymph nodes metastases which necessitated radiotherapy to his neck (50 cGy—CentiGrays dose) delivered in 33 fractions with chemotherapy. This led to radiation-induced thyroiditis and eventual progressive thyroid failure detected 2 years later on routine clinical follow-up.

| Date: | T1 | T2 | T3 | T4 | T5 |
|---|---|---|---|---|---|
| FT4: | 8, | 10, | 10.4, | 10, | 10 |
| TSH: | 7.49, | 4.07, | 5.85, | 5.36, | 4.11 |

Figure 13:
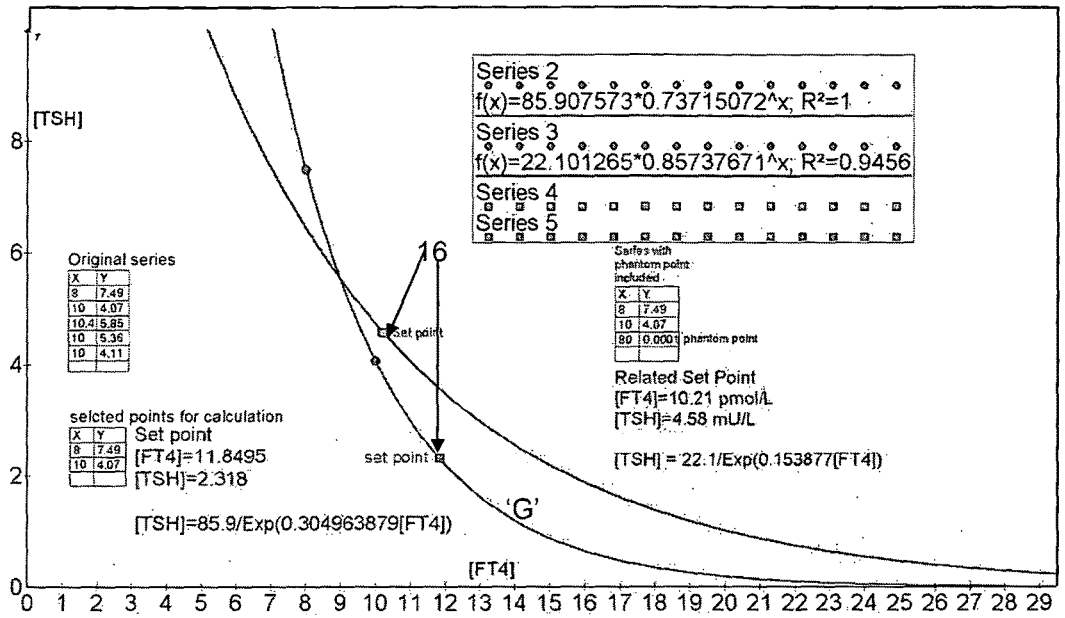
FIG. 13 is the clinical trial validation of example 4.

Overview of Two Possible Tracing Methods (See FIG. 13).

The plot (marked 'G') is based on two selected best possible points and results in a set point of [FT4]=11.85 pmol/L and a value for [TSH]=2.318 m U/L Tracing with an introduced phantom point of [FT4]=80 pmol/L and a belonging [TSH]=0.0001 mU/L the result is obtained in the form of the curve corresponding to a set point of [FT4]=10.21 pmol/L and a belonging [TSH]=4.58 mU/L. However, since this phantom point is assumed and may skew the calculations by deviating off the range compatible with the optimal operational characteristics of this math model, the plot marked 'G' is favoured over the other plot for the purposes of computing the HPT axis set point.

Thus, predicted set point is:

FT4~12 pmol/L

TSH~2.3 mIU/L

Compare this with his euthyroid TFTs over the 2 years prior to his nasopharyngeal carcinoma:

| Date: | T1 | T2 | T3 | T4 |
|---|---|---|---|---|
| FT4: | 13 | 13 | 14 | 14 |
| TSH: | 2.29 | 1.59 | 1.33 | 1.66 |

These TFTs would represent his approximate usual HPT axis set point. Taking the average of these 4 sets of results yield:
Average True Set Point:
FT4~13.5 pmol/L
TSH~1.7 mIU/L Although not in perfect agreement, the set point calculated falls within less than 2-folds of his true euthyroid set point, which is clinically far superior and more accurate than what his own oncologist had assumed his euthyroid TFTs to be, namely TSH between 4.07-5.36 mIU/L and FT4~10 pmol/L. While his oncologist replaced thyroid hormones using LT4 25 mcg once daily to get all his FT4 to about 10 pmol/L, all are significantly below his usual FT4 of around 13-14 pmol/L. Moreover, his usual TSH was between 1.3-2.3 mIU/L, whereas his TSH is mainly now hovering around 4-5+ mIU/L. This suggested that his present levels of FT4 and TSH, though both in the normal ranges are somewhat relatively more hypothyroid, leading him to feel a bit hypothyroid. Blind targeting of TFTs into the normal population ranges is still a very standard way of clinicians who usually accept this strategy as the goal of therapy. This however has its drawbacks as illustrated by this patient. Based on insights from the math model, I judged that the individual required slightly more L-T4, probably around 37.5 mcg to perhaps 50 mcg daily to get his FT4 and TSH closer to his original set points (which is considerably near to his computed set point).

Example 5

68 yr/Female

The patient is a case of non-toxic multinodular goiter that eventually had total thyroidectomy due to both compressive symptoms at the thoracic outlet and cosmetic reasons. Her TFTs done prior to surgery were essentially reflective of her HPT axis homeostatic set point:

| Day: | −124 | −17 | −1 |
|---|---|---|---|
| FT4: | 14 | 14 | 15 |
| TSH: | 0.33 | 0.46 | 0.41 |

Total thyroidectomy was performed on day 0. Subsequent post-op TFTs were:

| | FT4: | | | | | | |
|---|---|---|---|---|---|---|---|
| | 3 | 7 | 8 | 10 | 11 | 14 | 18 |
| TSH: | 75.21 | 66.48 | 20.62 | 7.9 | 0.93 | 0.83 | 0.02 |

Figure 14:
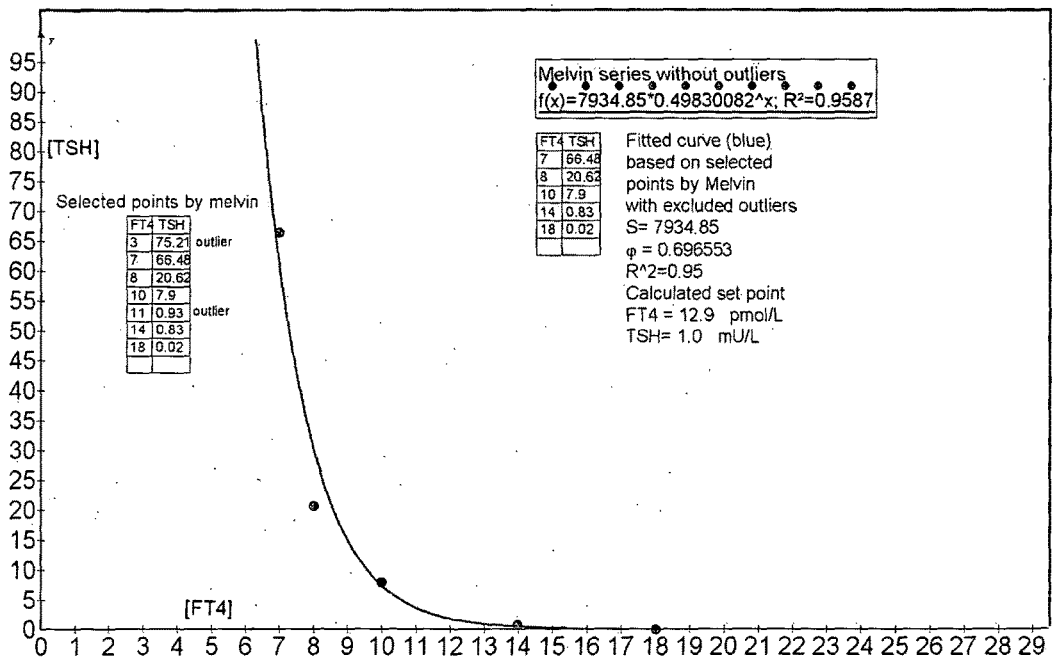
FIG. 14 is the clinical trial validation of example 5.

Using the method 10 (see FIG. 14), the predicted (computed) HPT set point: FT4~13, TSH=1

Comments: Her original (true) set point showed FT4~14, TSH~0.4. The calculated results matched reasonably well, given that variations in TSH are logarithmic and these values are within the same order of magnitude not exceeding 2-folds of the true set point.

Example 6 with the Example of Loop Gain Calculation

Data Analysis Patient Case Scenario—
59 yr/Female

Background of goitre (self-detected) but never sought medical advice. Co-morbidity of hypertension (well controlled). No pre-thyroid disease euthyroid TFTs.

In May 1997, found by polyclinic to have lethargy and cold intolerance. Investigations revealed Hashimoto's thyroiditis with elevated TSH and TPO Ab (44.5 U/mL) & Tg Ab (19 U/mL). Tc-99m scintigraphy on 15 May 2007 showed no nodules and uniform uptake (231 kCts in 272 seconds) ultrasound thyroid revealed heterogenous echotexture in keeping with Hashimoto's.

| Date: | 2 May 1997 | 17 Aug. 1998 | 16 Aug. 1999 | 26 Oct. 1999 | 24 Apr. 2002 | 3 May 2005 | 5 Oct. 2005 |
|---|---|---|---|---|---|---|---|
| FT4: | 11.5 | 10.6 | 12 | 14 | 13 | 13 | 16 |
| TSH: | 8.64 | 8.71 | 4.96 | 3.03 | 2.32 | 6.67 | 1.10 |
| LT4: | 25 | 50 | 50 | 50 | 50 | 75 | 100 |

| Date: | 23 Jan. 2006 | 21 Jun. 2006 | 19 Oct. 2006 | 12 Feb. 2007 | 14 May 2007 | 1 Oct. 2007 |
|---|---|---|---|---|---|---|
| FT4: | 14 | 13 | 12 | 15 | 14 | 11 |
| TSH: | 2.18 | 1.48 | 2.43 | 2.65 | 1.72 | 4.34 |
| LT4: | 100 | 100 | 100 | 100 | 100 | 100 |

| Date: | 28 Jul. 2008 | 10 Dec. 2010 | 6 May 2011 | 16 Mar. 2012 |
|---|---|---|---|---|
| FT4: | 13 | 18 | 17 | 15 |
| TSH: | 3.12 | 0.41 | 0.99 | 2.20 |
| LT4: | 100 | 100 | 100 | 100 |

The set point is based on an optimized data set with fitting quality=0.999. The set point is [FT4]=14.5 pmol/L and [TSH]=1.75 mU/L From the set point data [FT4]=14.5 pmol/L and [TSH]=1.75 mU/L the value of the loopgain $G_L$ is calculated based on the exponential thyroid model $$G_L = \frac{A\varphi}{e}$$

with $e = 2.7182$ $$A = \frac{[FT4]}{0.632} = \frac{14.5}{0.632} = 23$$

and $$\varphi = 0.40376$$

we find $$G_L = \frac{A\varphi}{e} = 3.4$$

Which complies to the condition of $G_L>1$

The loop gain at this set point is 3.4, and being greater than unity, the feedback loop is operational and stable in the control system of the patient's HPT axis.

It is to be understood that the above embodiments have been provided only by way of exemplification of this invention, and that further modifications and improvements thereto would be apparent to persons skilled in the relevant art and as such are deemed to fall within the broad scope and ambit of the present invention described. Furthermore although individual embodiments of the invention may have been described it is intended that the invention also covers combinations of the embodiments discussed.

The claims defining the invention are as follows:

1. A method of deriving a physiological homeostatic operating set point of an individual and adjusting the homeostatic measurements of the individual comprising:
   a. obtaining a dataset of predetermined number of homeostatic measurements of the individual;
   b. fitting the dataset of predetermined number of homeostatic measurements according to a negative exponential decay function in a manner so as to derive a multiplier parameter and a rotational parameter;
   c. identifying and setting a physiological homeostatic operating set point unique to the individual as the point corresponding to the point of maximum curvature on the fitted negative exponential decay function; and
   d. administering to the individual in need, a therapeutically effective amount of a compound to adjust the homeostatic measurements of the individual to the physiological homeostatic operating set point unique to the individual.

2. A method according to claim 1, wherein each of the predetermined number of homeostatic measurements is a thyroid-stimulating hormone [TSH] level and a corresponding free thyroxin [FT4] level of the individual, the homeostatic measurements obtained under controlled predetermined measurement conditions.

3. A method according to claim 1, wherein each of the predetermined number of homeostatic measurements is a thyroid-stimulating hormone [TSH] level and a corresponding free thyroxin [FT4] level of the individual, the homeostatic measurements obtained under controlled predetermined measurement conditions, and wherein the negative exponential decay function is mathematically expressed as the following formula:

$$[TSH] = \frac{S}{\exp(\varphi[FT4])}$$

Wherein S is the multiplier parameter; $\varphi$ is the rotational parameter; and exp denotes the exponential function.

4. A method according to claim 3, wherein the parameters S and $\varphi$ are calculated from a first and a second homeostatic measurements of the individual according to the following formula:

$$\varphi = \left(\frac{1}{[FT4]_1 - [FT4]_2}\right)\ln\left(\frac{[TSH]_2}{[TSH]_1}\right)$$

$$S=[TSH]_1\exp(\varphi[FT4]_1)=[TSH]_2\exp(\varphi[FT4]_2)$$

where the subscript 1 and 2 denote the first and second homeostatic measurement respectively.

5. A method according to claim 4, wherein for any measurement subsequent to the second homeostatic measurement, the parameters S and $\varphi$ are iteratively fine-tuned by using each subsequent homeostatic measurement with a first and a second homeostatic measurements.

6. A method according to claim 3, wherein the physiological homeostatic operating set point of the individual is determined according to the following formula:

$$[FT4]_{SP} = \frac{\ln(S\varphi\sqrt{2})}{\varphi}$$

$$[TSH]_{SP} = \frac{1}{\varphi\sqrt{2}}$$

Where $[FT4]_{SP}$ and $[TSH]_{SP}$ denote the physiological homeostatic operating set point of the individual.

7. A method according to claim 1, further comprising validating the physiological homeostatic operating set point of the individual based on a control system model.

8. A method according to claim 1, the method comprises calculating a loop gain of the obtained physiological homeostatic operating set point mathematically expressed as:—

$$G_L = \frac{A\varphi}{e}$$

Where $G_L$ is the calculated loop gain; e is the exponential constant e≈2.718;

$$A = \frac{[FT4]_{setpoint}}{0.632};$$

and $[FT4]_{setpoint}$ is the obtained [FT4] level of the operating set point for the individual, and accepting the obtained physiological homeostatic operating set point if the calculated $G_L$ is greater than 1.

9. A method according to claim 1, wherein the each of the predetermined number of homeostatic measurements comprises a thyroid-stimulating hormone (TSH) level and a corresponding triiodothyronine (T3) level.

10. A method according to claim 1 wherein each homeostatic measurement is obtained by measuring an amount of a homeostatic amino acid expression product with a detection reagent capable of hybridizing to the homeostatic amino acid expression product.

11. A method according to claim 10, wherein the detection reagent comprises a detectable marker and an antibody capable of hybridizing to a thyroid-stimulating hormone.

12. A method according to claim 1 wherein the therapeutically effective compound comprises thyroxin, active iodothyronines or iodothyroacetic acids.

* * * * *

UNITED STATES PATENT AND TRADEMARK OFFICE
CERTIFICATE OF CORRECTION

PATENT NO. : 10,204,708 B2  
APPLICATION NO. : 14/443276  
DATED : February 12, 2019  
INVENTOR(S) : Sam L. Goede et al.

Page 1 of 1

It is certified that error appears in the above-identified patent and that said Letters Patent is hereby corrected as shown below:

On the Title Page

Item (71) should read:  
(71) Applicants:  
Agency for Science, Technology and Research, Singapore (SG); Sam L. Goede, Stompetoren (NL); Johannes W. Dietrich, Hattingen (DE); Khee Shing Melvin Leow, Singapore (SG)

Signed and Sealed this  
Twenty-second Day of October, 2019

Andrei Iancu  
*Director of the United States Patent and Trademark Office*